(12) United States Patent
Harvey et al.

(10) Patent No.: US 6,849,400 B1
(45) Date of Patent: Feb. 1, 2005

(54) METHODS FOR DETECTING AND MEASURING SPLICED NUCLEIC ACIDS

(75) Inventors: Richard C. Harvey, San Diego, CA (US); Paul Scott Eastman, Moraga, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 09/121,239

(22) Filed: Jul. 23, 1998

Related U.S. Application Data
(60) Provisional application No. 60/053,509, filed on Jul. 23, 1997.

(51) Int. Cl.[7] .................................................. C12Q 1/68
(52) U.S. Cl. ...................... 435/6; 435/91.2; 536/23.1; 536/24.3; 536/24.31
(58) Field of Search .................. 435/6, 91.1, 91.2, 435/91.21, 91.51; 536/23.1, 24.3, 24.33, 25.3

(56) References Cited

U.S. PATENT DOCUMENTS

| | | | |
|---|---|---|---|
| 4,599,305 A | 7/1986 | Witte et al. | 435/7.23 |
| 4,681,840 A | 7/1987 | Stephenson et al. | 435/6 |
| 4,683,195 A | 7/1987 | Mullis et al. | 435/6 |

(List continued on next page.)

FOREIGN PATENT DOCUMENTS

| | | |
|---|---|---|
| DE | 4447015 | 12/1994 |
| EP | 0181635 | 5/1986 |
| EP | 0364953 | 4/1990 |
| EP | 0846776 A2 | 6/1998 |
| WO | 8808036 | 10/1988 |
| WO | 8903675 | 5/1989 |
| WO | 8904373 | 5/1989 |
| WO | 9708339 | 3/1997 |
| WO | 9850583 | 11/1998 |

OTHER PUBLICATIONS

Qiagen Oligotex Direct mRNA Handbook Protocol, Nov. 1994, pp. 1–51.*
Eskola et al., Clin Biochem, vol. 27, p 373–379, Oct. 1994.*
Goddard et al, Science, vol. 254 (5036) p 1371–4, Nov. 1991.*
von Lindern et al, Mol Cell Biol, vol. 12(8) pp 3346–3355, Aug. 1992.*
Roy Sooknanan et al., Detection and direct sequence indentification of BCR–ALB mRNA in Ph+ chronic myeloid leukemia, Experimental Hematology 21: pp. 1719–1724, 1993.*
Oligotex for efficient poly A+ mRNA purification, pp. 61–62, 43–47 and 75, 1998.*
Bakhshi et al., "Mechanism of the t(14;18) chromosomal translocation: Structural analysis of both derivative 14 and 18 reciprocal partners", *Proc. Natl. Acad. Sci, USA*, 84:2396–2400 (1987).
Bakhshi et al., "Cloning the Chromosomal Breakpoint of t(14;18) Human Lymphomas: Clustering around $J_{38}$ on Chromosome 14 and near a Transcriptional Unit on 18", *Cell*, 41:899–906 (1985).
Barr et al., "Localization of the Rhabdomyosarcoma t(2;13) Breakpoint on a Physical Map of Chromosome 13", *Genomics*, 11:941–947 (1991).
Chen et al., "Breakpoint Clustering in t (4;11) (q21;q23) Acute Leukemia", *Blood*, 78(10):2498–2504 (1991).

(List continued on next page.)

*Primary Examiner*—John L. LeGuyader
*Assistant Examiner*—Terra C. Gibbs
(74) *Attorney, Agent, or Firm*—Christine A. Gritzmache; Carlos A. Fisher

(57) ABSTRACT

The invention includes methods of detecting and measuring the amount of one or more species of bcr-abl spliced mRNA present in the sample, following nucleic acid amplification.

23 Claims, 3 Drawing Sheets

U.S. PATENT DOCUMENTS

| | | | | |
|---|---|---|---|---|
| 4,710,465 | A | | 12/1987 | Weissman et al. ............. 435/6 |
| 4,874,853 | A | | 10/1989 | Rossi ...................... 536/24.31 |
| 4,999,290 | A | | 3/1991 | Lee ................................ 435/6 |
| 5,024,934 | A | | 6/1991 | Lee ................................ 435/6 |
| 5,057,410 | A | | 10/1991 | Kawasaki et al. ............. 435/6 |
| 5,066,792 | A | * | 11/1991 | Saunders et al. ........ 536/24.31 |
| 5,085,983 | A | | 2/1992 | Scanlon .......................... 435/6 |
| 5,112,734 | A | | 5/1992 | Kramer et al. .................. 435/6 |
| 5,149,628 | A | | 9/1992 | Croce ............................. 435/6 |
| 5,198,338 | A | | 3/1993 | Croce ............................. 435/6 |
| 5,202,429 | A | | 4/1993 | Tsujimoto et al. ......... 536/23.5 |
| 5,242,795 | A | | 9/1993 | Croco ............................ 435/6 |
| 5,369,008 | A | | 11/1994 | Arlinghaus et al. ........ 435/7.23 |
| 5,399,491 | A | * | 3/1995 | Kacian et al. ............ 435/91.21 |
| 5,424,413 | A | * | 6/1995 | Hogan et al. ............ 536/24.31 |
| 5,459,251 | A | | 10/1995 | Tsujimoto et al. ......... 536/23.5 |
| 5,480,784 | A | | 1/1996 | Kacian et al. ............ 435/91.21 |
| 5,482,834 | A | * | 1/1996 | Gillespie ........................ 435/6 |
| 5,487,970 | A | * | 1/1996 | Rowley et al. ................ 435/6 |
| 5,529,925 | A | * | 6/1996 | Morris et al. ............ 435/252.3 |
| 5,538,846 | A | | 7/1996 | Meeker ......................... 435/6 |
| 5,538,869 | A | | 7/1996 | Siciliano et al. ........... 435/91.2 |
| 5,547,838 | A | | 8/1996 | Nisson et al. .................. 435/6 |
| 5,567,586 | A | | 10/1996 | Croce ............................. 435/6 |
| 5,580,727 | A | * | 12/1996 | Ohki et al. ..................... 435/6 |
| 5,614,391 | A | | 3/1997 | Franciskovich et al. ... 435/91.3 |
| 5,633,135 | A | | 5/1997 | Croce et al. .................... 435/6 |
| 5,643,730 | A | | 7/1997 | Banker et al. .................. 435/6 |
| 5,650,278 | A | | 7/1997 | Barr et al. ...................... 435/6 |
| 5,663,319 | A | | 9/1997 | Bittner et al. ............... 536/24.3 |
| 5,728,822 | A | * | 3/1998 | Macfarlane .............. 536/25.41 |
| 5,731,153 | A | | 3/1998 | Lucas et al. .................... 435/6 |
| 5,756,696 | A | | 5/1998 | Gray et al. ................. 536/23.1 |
| 5,830,711 | A | * | 11/1998 | Barany et al. |
| 5,858,682 | A | * | 1/1999 | Gruenwald et al. .......... 435/7.1 |
| 5,908,750 | A | * | 6/1999 | Reed et al. ..................... 435/6 |
| 6,071,698 | A | | 6/2000 | Beck |
| 6,300,068 | B1 | * | 10/2001 | Burg et al. |

OTHER PUBLICATIONS

Cleary et al., "Nucleotide sequence of a t(14;18) chromosomal breakpoint in follicular lymphoma and demonstration of a breakpoint–cluster region near a transcriptionally active locus on chromosome 18", *Proc. Natl. Acad. Sci. USA*, 82:7439–7443 (1985).

Cleary et al., "Cloning and Structural Analysis of cDNAs for bcl–2 and a Hybrid bcl–2/Immunoglobulin Transcript Resulting from the t(14;18) Transolcation", *Cell*, 47:19–28 (1986).

Crescenzi et al., "Thermostable DNA polymerase chain amplification of t (14;18) chromosome breakpoints and detection of minimal residual disease", *Proc. Natl. Acad. Sci. USA*, 85:4869–4873 (1988).

Domer et al., "Acute mixed–lineage leukemia t (4;11) (q21;q23) generates an MLL–AF4 fusion product", *Proc. Natl. Acad. Sci USA*, 90:7884–7888 (1993).

Groffen et al., "Philadelphia Chromosomal Breakpoints Are Clustered within a Limited Region, bcr, on Chromosome 22", *Cell*, 36:93–99 (1984).

Gu et al., "Sequence Analysis of the Breakpoint Cluster Region in the ALL–1 Gene Involved in Acute Leukemia", *Cancer Research*, 54:2327–2330 (1994).

Hermans et al., "Unique Fusion of bcr and c–ab1 Genes in Philadelphia Chromosome Positive Acute Lymphoblastic Leukemia", *Cell*, 51:33–40 (1987).

Kakizuka et al., "Chromosomal Translocation t (15;17) in Human Acute Promyelocytic Leukemia Fuses RARα with a Novel Putative Transcription Factor, PML", *Cell*, 66:663–674 (1991).

Kamps et al., "A New Homeobox Gene Contributes the DNA Binding Domain of the t (1;19) Translocation Protein in Pre–B ALL", *Cell*, 60:547–555 (1990).

Kawasaki et al., "Diagnosis of chronic myeloid and acute lymphocytic leukemias by detection of leukemia–specific mRNA sequences amplified in vitro", *Proc. Natl. Acad. Sci USA*, 85:5698–5702 (1988).

Lund et al., "Assessment of methods for covalent binding of nucleic acids to magnetic beads, Dynabeads™, and the characteristics of the bound nucleic acids in hybridization reactions", *Nucleic Acids Research*, 16(22):10861–10880 (1988).

Mellentin et al., "The Gene for Enhancer Binding Proteins E12/E47 Lies at the t(1;19) Breakpoint in Acute Leukemias", *Science*, 246:379–382 (1989).

Mitelman et al., "Report of the committee on chromosome changes in neoplasia", *Cytogenet Cell Genet*, 55:358–386 (1990).

Nakamura et al., "Genes on chromosomes 4, 9, and 19 involved in 11q23 abnormalities in acute leukemia share sequence homology and/or common motifs", *Proc. Natl. Acad. Sci. USA*, 90:4631–4635 (1993).

Nourse et al., "Chromosomal Translocation t (1;19) Results In Synthesis of a Homeobox Fusion mRNA That Codes for a Potential Chimeric Transcription Factor", *Cell*, 69:535–545 (1990).

Pers ing et al., In Vitro Nucleic Acid Amplification Techniques, *Diagnostic Molecular Microbiology: Principles and Applications*, (American Society for Microbiology—WA D.C.), Chpt. 3, pp. 51–87.

Sacchi et al., "Hu–ets–1 and Hu–ets–2 Genes Are Transposed in Acute Leukemias with (4;11) and (8;21) Translocations", *Science*, 231:379–382 (1986).

Sawyers et al., "Molecular relapse in chronic myelogenous leukemia patients after bone marrow transplantation detected by polymerase chain reaction", *Proc. Natl. Acad. Sci USA*, 87:563–567 (1990).

Selleri, et al., "Molecular localization of the t (11;22) (q24;q12) translocation of the Ewing sarcoma by chromosomal in situ suppression hybridization", *Proc. Natl. Acad. Sci USA*, 88:887–891 (1991).

Shtivelman et al., "Fused transcript of abl and bcr genes in chronic myelogenous leukaemia", *Nature*, 315:550–554 (1985).

Sooknanan et al., "Detection and direct sequence identification of BCR–ABL mRNA in Ph⁺ chronic myeloid leukemia", *Experimental Hematology*, 21:1719–1724 (1993).

Tkachuk et al., "Detection of bcr–ab1 Fusion in Chronic Myelogeneous Leukemia by in Situ Hybridization", *Science*, 250:559–562 (1990).

Tsujimoto et al., "Molecular Cloning of the Chromosomal Breakpoint of B–Cell Lymphomas and Leukemias with the t (11;14) Chromosome Translocation", *Science*, 224:1403–1406 (1984).

von Lindern et al., "The Translocation (6;9), Associated with a Specific Subtype of Acute Myeloid Leukemia, Results in the Fusion of Two Genes, dek and can, and the Expression of a Chimeric, Leukemia–Specific dek–can mRNA", *Molecular and Cellular Biology*, 12(4):1687–1697 (1992).

Walker et al., "Isothermal in vitro amplification of DNA by a restriction enzyme/DNA polymerase system", *Proc. Natl. Acad. Sci USA*, 89:392–396 (1992).

Ziemin–van der Poel et al., "Identification of a gene, MLL, that spans the breakpoint in 11q23 translocations associated with human leukemias", *Proc. Natl. Acad. Sci. USA*, 88:10735–10739 (1991).

Burnett, et al., "Molecular Analysis of a t(11;14) (q23;q11) From a Patient With Null–Cell Acute Lymphoblastic Leukemia", *Genes, Chromosomes & Cancer*, 7:38–46 (1993).

Sarris, et al., "Genomic DNA Amplification and the Detection of t(2;5) (p23;q35) in Lymphoid Neoplasma", *Leukemia and Lymphoma*, 29:507–514 (1998).

Estrov et al., "Heterogeneity in Lineage Derivation of Philadelphia–positive Acute Lymphoblastic Leukemia Expressing p190BCR–ABL or p120BCR–ABL: Determination by Analysis of Individual Colonies with the Polymerase Chain Reaction", Cancer Res., Jul. 1993; 53(14):3289–93.

Harvey et al., "Diagnosis and Monitoring of CML Using HPA and TMA (an Isothermal Amplification System)", Proceedings of the Molecular Pathology Conference, Rockville, Maryland, Nov. 11–13, 1994.

Langabeer et al., "TMA/HPA for the Detection fo BCR–ABL in CML", Leukemia, 2002, 16:393–9.

Morris et al., "Fusion of a Kinase Gene, ALK, to a Nucleolar Protein Gene, NPM, in Non–Hodgkin's Lymphoma", Science, Mar. 1994, 263(5151):1281–4.

Radich et al., "Polymerase Chain Reaction Detection of the BCR–ABL Fusion Transcript After Allogeneic Marrow Transplantation for Chronic Myeloid Leukemia: Results and Implications in 346 Patients", Blood, May 1995, 85(9):2632–8.

\* cited by examiner

TCCGGGAGCAGCAGAAGAAGTGTTTCAGAAGCTTCTCCCT

GACATCCGTGGAGCTGCAGATGCTGACCAACTCGTGTGTG

AAACTCCA*GACTGTCCACAGCATTCCGCTGACC*ATCAACA

AGGAAGATGATGAGTCTCCGGGGCTCTATGGGTTTCTGAA

TGTCATCGTCCACTCAGCCACTGGATTTAAGCAGAGTTCA

AAAGCCCTTCAGCGGCCAGTAGCATCTGACTTTGAGCCTC

AGGGTCTGAGTGAAGCCGCTCGTTGGAACTCCAAGGAAAA

CCTTCTCGCTGGACCCAGTGAAAATGACCCCAACCTTTTC

GTTGCACTGTATGATTTTGTGGCCAGTGGA

FIG. 2

ACCTATTATTACTTTATGGGGCAGCAGCCTGGAAAAGTAC

TTGGGGACCAAAGAAGGCCAAGCTTGCCTGCCCTGCATTT

TATCAAAGGAGCAGGGAAGAAGGAATCATCGAGGCATGGG

GGTCCACACTGCAATGTTTTTGTGGAACATGAAGCCCTTC

AGCGGCCAGTAGCATCTGACTTTGAGCCTCAGGGTCTGAG

TGAAGCCGCTCGTTGGAACTCCAAGGAAACCTTCTCGCT

GGACCCAGTGAAAATGACCCCAACCTTTCGTTGCACTGTA

TGATTTTGTGGCCAGTGGA

FIG. 3

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
         (A) LENGTH: 54 base pairs
         (B) TYPE: nucleic acid
         (C) STRANDEDNESS: single
         (D) TOPOLOGY: linear (xi) SEQUENCE DESCRIPTION: SEQ ID NO:1:

TAAATTAATA CGACTCACTA TAGGGAGACT CAGACCCTGA GGCTCAAAGT CAGA        54

(2) INFORMATION FOR SEQ ID NO:2:

(i) SEQUENCE CHARACTERISTICS:
         (A) LENGTH: 54 base pairs
         (B) TYPE: nucleic acid
         (C) STRANDEDNESS: single
         (D) TOPOLOGY: linear (xi) SEQUENCE DESCRIPTION: SEQ ID NO:2:

UAAAUUAAUA CGACUCACUA UAGGGAGACU CAGACCCUGA GGCUCAAAGU CAGA        54

(2) INFORMATION FOR SEQ ID NO:3:

(i) SEQUENCE CHARACTERISTICS:
         (A) LENGTH: 54 base pairs
         (B) TYPE: nucleic acid
         (C) STRANDEDNESS: single
         (D) TOPOLOGY: linear (xi) SEQUENCE DESCRIPTION: SEQ ID NO:3:

TCTGACTTTG AGCCTCAGGG TCTGAGTCTC CCTATAGTGA GTCGTATTAA TTTA        54

(2) INFORMATION FOR SEQ ID NO:4:

(i) SEQUENCE CHARACTERISTICS:
         (A) LENGTH: 54 base pairs
         (B) TYPE: nucleic acid
         (C) STRANDEDNESS: single
         (D) TOPOLOGY: linear (xi) SEQUENCE DESCRIPTION: SEQ ID NO:4:

UCUGACUUUG AGCCUCAGGG UCUGAGUCUC CCUAUAGUGA GUCGUAUUAA UUUA        54

(2) INFORMATION FOR SEQ ID NO:5:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (xi) SEQUENCE DESCRIPTION: SEQ ID NO:5:

GACCAACTCG TGTGTGAAAC TCCA                                        24

(2) INFORMATION FOR SEQ ID NO:6:

(i) SEQUENCE CHARACTERISTICS:
         (A) LENGTH: 24 base pairs
         (B) TYPE: nucleic acid
         (C) STRANDEDNESS: single -continued (D) TOPOLOGY: linear (xi) SEQUENCE DESCRIPTION: SEQ ID NO:6:

GACCAACUCG UGUGUGAAAC UCCA                                          24

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:7:

TGGAGTTTCA CACACGAGTT GGTC                                          24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:8:

UGGAGUUUCA CACACGAGUU GGUC                                          24

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:9:

GACTGTCCAC AGCATTCCGC TGACC                                         25

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:10:

GACUGUCCAC AGCAUUCCGC UGACC                                         25

(2) INFORMATION FOR SEQ ID NO:11:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:11:

GGTCAGCGGA ATGCTGTGGA CAGTC                                         25

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:12:

GGUCAGCGGA AUGCUGUGGA CAGUC                                          25

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:13:

CAAAGGAGCA GGGAAGAAGG                                                20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:14:

CCTTCTTCCC TGCTCCTTTG                                                20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:15:

CCUUCUUCCC UGCUCCUUUG                                                20

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:16:

GTGGAACATG AAGCCCTTCA GCGG                                           24

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

GUGGAACAUG AAGCCCUUCA GCGG                                           24

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single (D) TOPOLOGY: linear (xi) SEQUENCE DESCRIPTION: SEQ ID NO:18:

CCGCTGAAGG GCTTCATGTT CCAC                                          24

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:19:

CCGCUGAAGG GCUUCAUGUU CCAC                                          24

(2) INFORMATION FOR SEQ ID NO:20:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:20:

ACTCAGACCC TGAGGCTCAA AGTCAGA                                       27

(2) INFORMATION FOR SEQ ID NO:21:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:21:

ACUCAGACCC UGAGGCUCAA AGUCAGA                                       27

(2) INFORMATION FOR SEQ ID NO:22:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:22:

TCTGACTTTG AGCCTCAGGG TCTGAGT                                       27

(2) INFORMATION FOR SEQ ID NO:23:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:23:

UCUGACUUUG AGCCUCAGGG UCUGAGU                                       27

(2) INFORMATION FOR SEQ ID NO:24:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (xi) SEQUENCE DESCRIPTION: SEQ ID NO:24:

| | | | | | |
|---|---|---|---|---|---|
| TCCGGGAGCA | GCAGAAGAAG | TGTTTCAGAA | GCTTCTCCCT | GACATCCGTG | GAGCTGCAGA | 60 |
| TGCTGACCAA | CTCGTGTGTG | AAACTCCAGA | CTGTCCACAG | CATTCCGCTG | ACCATCAACA | 120 |
| AGGAAGATGA | TGAGTCTCCG | GGGCTCTATG | GGTTTCTGAA | TGTCATCGTC | CACTCAGCCA | 180 |
| CTGGATTTAA | GCAGAGTTCA | AAAGCCCTTC | AGCGGCCAGT | AGCATCTGAC | TTTGAGCCTC | 240 |
| AGGGTCTGAG | TGAAGCCGCT | CGTTGGAACT | CCAAGGAAAA | CCTTCTCGCT | GGACCCAGTG | 300 |
| AAAATGACCC | CAACCTTTTC | GTTGCACTGT | ATGATTTTGT | GGCCAGTGGA | | 350 |

(2) INFORMATION FOR SEQ ID NO:25:

(i) SEQUENCE CHARACTERISTICS:
        (A) LENGTH: 299 base pairs
        (B) TYPE: nucleic acid
        (C) STRANDEDNESS: single
        (D) TOPOLOGY: linear (xi) SEQUENCE DESCRIPTION: SEQ ID NO:25:

| | | | | | |
|---|---|---|---|---|---|
| ACCTATTATT | ACTTTATGGG | GCAGCAGCCT | GGAAAAGTAC | TTGGGGACCA | AAGAAGGCCA | 60 |
| AGCTTGCCTG | CCCTGCATTT | TATCAAAGGA | GCAGGGAAGA | AGGAATCATC | GAGGCATGGG | 120 |
| GGTCCACACT | GCAATGTTTT | TGTGGAACAT | GAAGCCCTTC | AGCGGCCAGT | AGCATCTGAC | 180 |
| TTTGAGCCTC | AGGGTCTGAG | TGAAGCCGCT | CGTTGGAACT | CCAAGGAAAA | CCTTCTCGCT | 240 |
| GGACCCAGTG | AAAATGACCC | CAACCTTTCG | TTGCACTGTA | TGATTTTGTG | GCCAGTGGA | 299 |

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:26:

GGAATCATCG AGGCATGG                                                  18

(2) INFORMATION FOR SEQ ID NO:27:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

CACTCAGCCA CTGGATTTAA GCAGAG                                    26

METHODS FOR DETECTING AND MEASURING SPLICED NUCLEIC ACIDS

This application claims the benefit of U.S. Provisional Application No. 60/053,509, filed Jul. 23, 1997.

FIELD OF THE INVENTION

This invention relates to detection and measurement of nucleic acids, preferably mRNA, derived from biological sources, and specifically relates to methods for specifically detecting spliced mRNA, including spliced mRNA resulting from normal mRNA intracellular processing and atypically spliced mRNA resulting from chromosomal translocation events such as occur in some cancerous cells.

BACKGROUND OF THE INVENTION

Molecular biology methods have allowed researchers to investigate the genetic basis of disease processes and identify molecular events, such as aberrant genetic splicing, deletions, insertions, substitutions and amplifications responsible for genetic defects associated with some diseases, such as cancer. Certain aberrant genetic splicing events are nonrandom and characteristic of particular diseases.

In eukaryotes, the genetic information in DNA is present in chromosomes contained within a nucleus. Some viruses also contain chromosome-like genetic structures. The genetic information contained within one strand of DNA depends on the sequence of bases (i.e., "bass sequence" or "nucleotide sequence") where the bases are adenine (A), guanine (G), cytosine (C) and thymine (T). DNA encodes complementary messenger ribonucleic acid (mRNA) sequences, in which T is replaced with uracil (U) and the 5' to 3' nucleotide sequence specifies the amino acid sequence of the encoded protein. Eukaryotic genes generally include noncontiguous coding regions ("exons") separated by intervening non-coding regions ("introns"). Nuclear transcription synthesizes a precursor mRNA (pre-mRNA) complementary to the coding DNA strand, including introns and exons. Pro-mRNA is processed to eliminate the introns by cleaving and splicing the RNA to covalently link the exons and concurrently excise the introns. The resulting mature mRNA exits the nucleus into the cytoplasm where translation occurs during protein synthesis.

Nucleic acid splicing also occurs in the life cycle of many viruses. Some viruses integrate their nucleic acid into a host cell's DNA as a provirus using a splicing mechanism in which the host DNA is cleaved followed by insertion and ligation of the viral nucleic acid ends to the host DNA ends. Viral insertion often occurs at a specific locus or related loci in the host chromosome characteristic of the virus or viral family. A pathogenic provirus present in a target cell population may be associated with a specific condition or disease. Insertion of a provirus within a chromosomal exon or near an intron-exon border may lead to the production of an abnormal version of a normally transcribed mRNA and/or translated protein, with subsequent deleterious effects on the cell.

Chromosomal translocations are genetic recombination events associated with certain cancers, such as some leukemias and lymphomas. In some translocations, two different chromosomes reassemble by reciprocal genetic exchange between the chromosomes forming two hybrid chromosomes, each including portions of two normal chromosomes. Other translocations are intrachromosomal, joining normally noncontiguous regions of the same chromosome. A "breakpoint junction" of the translocation refers to a joining point of sequences derived from normally separated chromosomal locations. In some translocations, the breakpoint junctions are clustered in conserved locations within one or both of two chromosomes. Translocations occurring within a genetic coding region may result in atypical mRNA having discrete regions, such as a 5' portion derived from one chromosomal location and a 3' portion derived from another chromosomal location. Such novel transcription products are known as "fusion transcripts" or "fusion mRNA."

One family of translocation events are characteristic of patents having chronic myelogenous leukemia ("CML"). The translocations occur between human chromosomes 9 and 22 (referred to as "t(9;22)"), and the resulting shortened chromosome 22 is known as the Philadelphia chromosome or $Ph^1$. The t(9;22) events link portions of the abl gene of chromosome 9, and the "breakpoint cluster region" or bcr gene of chromosome 22. A cDNA prepared from an about 8 kb fusion mRNA isolated from a $Ph^1$-positive cell line has been sequenced, revealing both abl and bcr sequences that code for a fusion protein having a tyrosine kinase activity (Shtivelman et al., *Nature* 315:550–554, 1985). The translocation occurred between the abl exon 2 and the bcr b3 region. Antibody-detection of an altered Abl protein having a molecular weight higher than that of normal Abl protein has been used for detecting $Ph^1$-positive cells, diagnostic of CML, as described in U.S. Pat. No. 4,599,305 to Witte et al.

A subtype of acute lymphoblastic leukemia (ALL) is also characterized by a translocation between chromosomes 22 and 9, within a bcr region about 50 kb 5' of the CML-associated bcr region. These ALL-associated translocations occur within the putative first intron of the bcr region, giving rise to a novel chimeric mRNA containing a splice between the bcr b1 of chromosome 22 and the abl exon 2 of chromosome 9, producing a novel fusion protein (Hermans et al., *Cell* 51:33–40, 1987). ALL-associated translocations on chromosome 22 have been detected with probes specific for a portion of the bcr gene as disclosed in European Pat. Publication No. EP 0 364 953 by Nakamura et al.

Chromosomal translocations involving chromosomes 8 and 21 have been associated with up to 40% of reported cases of pediatric acute myelogenous leukemia ("AML") with the FAB-M2 morphology. The breakpoints on both chromosomes are variable, but generally result in a common fusion transcript containing 5' portions of the AML1 gene of chromosome 21 and 3' portions of the ETO gene of chromosome 8, which gives rise to a fusion protein (U.S. Pat. No. 5,580,727 to Ohki et al.).

Other chromosomal translocations associated with diseases such as lymphomas and leukemias are the t(15;17) translocation (ALL), and the t(12;21), t(4;11) and the t(1;19) translocations (AML).

The detection of chimeric DNA and/or RNA and/or fusion proteins associated with conditions and diseases such as those exemplified above would be useful in confirming initial diagnosis, in monitoring a patient's response to treatment, and in providing early warning of any recurrence of disease after a period of remission. One problem previously limiting the ability to detect chimeric nucleic acids or proteins has been the extremely small numbers of cells that are present at different stages of the condition, especially following remission or in a non-acute phase. Immunological techniques are not generally sensitive enough to detect such small amounts of analyte in a sample. The prognosis for patients having conditions associated with chromosomal translocations, including recurrence of the condition, is usually more favorable with early diagnosis compared to later diagnosis.

Methods for the diagnosis of conditions associated with chromosomal translocations, such as CML and ALL have been reported. U.S. Pat. No. 4,681,840 to Stephenson et al. and PCT Pub. No. WO 85/03297 disclose DNA and hybridization methods for direct detection of CML-associated Philadelphia chromosome abnormalities using a chromosomal DNA-derived probe containing sequences complementary to the bcr region. CML-associated t(9;22) translocations resulting from splicing events that join bcr b2 or b3 with abl exon 2 can be detected by amplifying the fusion mRNA and hybridizing thereto synthetic oligonucleotide probes specific for these spliced sequences, as described in U.S. Pat. No. 4,874,853 to Rossi et al. and European Pat. Pub. No. 0338713. Methods of detecting unique aberrant gene transcripts of a targeted genomic abnormality by hybridizing the RNA with one or more synthetic DNA oligonucleotides complementary to RNA sequences encoded by the $Ph^1$ chromosome, thereby forming an RNA-DNA heteroduplex resistant to enzymatic degradation, followed by PCR amplification and DNA detection as an indication of the presence of unique aberrant gene transcripts are described in U.S. Pat. No. 4,999,290 to Lee. The DNA oligonucleotides include bcr b2 and/or b3 and abl sequences. DNA sequences for detecting and identifying chromosomal aberrations in tumor DNA containing the ALL-1 breakpoint region of human chromosome 11 (e.g., t(9;11 translocations) using probe hybridization in a variety of methods (Southern or Northern blotting or in situ hybridization) are disclosed in U.S. Pat. Nos. 5,567,586 and 5,633,136 to Croce et al.

Methods for detecting translocations using junction probes are limited to detecting mRNA or DNA resulting from specific fusion events because each detection probe is directed to a specific breakpoint junction. For translocations such as those associated with CML in which a large number of breakpoints can occur within a small area of the bcr gene, detection of mRNA resulting from each such fusion would require use of a different breakpoint junction probe. Also, point mutations that may limit probe hybridization are sometimes found within a few bases of a splice junction. Furthermore, other chromosomal rearrangement events such as deletions or insertions within the breakpoint cluster region may also produce less-common CML-associated transcripts. These events would result in mRNA or DNA species that would not be detected by using a common breakpoint junction probe.

U.S. Pat. No. 5,487,970 to Rowley et al. discloses methods for the detection of chromosome 11 (11q22) translocations, using a breakpoint probe such as mentioned above, or a method employing fluorescent in situ hybridization (FISH). In the FISH method, two fluorescently-labeled probes directed to 11 q22 chromosomal regions flanking a commonly-found breakpoint are hybridized to chromosomes in situ which are then are observed using a microscope illuminated at the light wavelength at which the fluors absorb. Cells in which the label is present only on chromosome 11 are classified as normal, whereas cells in which the label appears on different chromosomes are identified as possessing a translocation. This method requires a relatively large cell population to screen if the translocation is not present in many cells in the sample. The disclosed probes include restriction endonuclease fragments that can hybridize to chromosomal translocations involving the ALL-1 gene of chromosome 11 in a FISH or Southern blot format. Other methods for detecting CML-associated translocations using FISH involve probes derived from species-specific DNA regions between repeat segments ("inter-Alu" sequences) as disclosed in U.S. Pat. No. 5,538,869 to Siciliano et al.

The aforementioned methods rely on direct detection of the chimeric RNA or DNA by nucleic acid hybridization without signal or target amplification. Therefore, these detection methods require a relatively large number of the target cells bearing the chromosomal rearrangement in the tissue, blood, or other body fluid from which the sample is taken. However, large numbers of abnormal cells are not generally present in a biological sample when the disease appears to be in remission or is in a chronic non-acute state. Thus, by the time sufficient amounts of cells bearing genetic abnormalities are present to permit direct detection, a patient's treatment options may be limited.

Other methods of target nucleic acid detection use amplification to obtain multiple copies of a target nucleic acid (either or both of the complementary strands) or a reporter molecule to increase detection sensitivity. A variety of nucleic amplification methods are known to those skilled in the art (e.g., see Persing, D. H., "In Vitro Nucleic Acid Amplification Techniques" in *Diagnostic Medical Microbiology: Principles and Applications* 51 (Persing et al., Ed., 1993)).

Polymerase chain reaction (PCR) permits detection of small amounts of DNA present in a sample by amplifying the DNA target using two or more primers and a repeated series of thermal denaturation, primer annealing and synthesis steps (U.S. Pat. No. 4,683,195 to Mullis et al.; *PCR Protocols: A Guide to Methods and Applications*, Innes, M. A. et al., Ed., Academic Press, Inc., 1990, San Diego, Calif.). Generally, a first primer hybridizes to a specific region of the target nucleic acid, and a second primer hybridizes to the opposite strand of the target DNA 5' to the binding site of the first primer to produce by enzymatic means a series of primer extension products that exponentially amplify the region between the primers.

The ligase chain reaction (LCR) uses two complementary sets of short DNA oligonucleotides that hybridize to adjacent regions of a target nucleic acid and the oligonucleotides are then covalently linked by using a DNA ligase (European Pat. No. 0320308). By employing repeated cycles of thermal denaturation, hybridization and ligation an accumulated double-stranded ligated oligonucleotide product can be detected, indicating the presence of the target nucleic acid in a sample.

Strand displacement amplification (Walker et al., *Proc. Natl. Acad. Sci. USA* 89:392–396,1992), employs oligonucleotide primers that contain restriction endonuclease cleavage sites and hybridize to opposite strands of a target nucleic acid duplex (i.e., on the + and − sense strands) on either side of the sequence to be amplified. DNA polymerase-mediated primer extension using three deoxynucleoside triphosphates (dNTP) and a single dNTP[α]S produces a duplex hemiphosphorothioated primer extension product, which is nicked rather than cut by restriction endonuclease. Then, the 3' end of the nick is extended by a DNA polymerase that simultaneously displaces the non-hemiphosphorothioated strand. Each displaced strand of one sense can serve as a template for the binding of oligonucleotide primers of the opposite sense, resulting in the geometric accumulation of double stranded nucleic acids.

Another nucleic acid amplification method employs an RNA replicase (Qβ replicase) capable of amplifying the probe itself (e.g., see U.S. Pat. No. 5,112,734 to Kramer et al.)

Transcription based amplification systems employ an RNA polymerase to make RNA transcripts of a target region (see U.S. Pat. Nos. 5,480,784 and 5,399,491 to Kacian & Fultz). One method, termed transcription-mediated amplification (TMA), uses a promoter-primer that hybridizes to a target nucleic acid in the presence of a reverse transcriptase and an RNA polymerase to form a double stranded promoter. Then, RNA transcripts are produced which become templates for further rounds of TMA in the presence of a second primer capable of hybridizing to the RNA transcripts. Unlike PCR and other methods that require heat denaturation, TMA is an isothermal amplification method that uses an RNAse H activity to digest the RNA strand of an RNA-DNA hybrid, thereby making the DNA strand available for hybridization with a primer or promoter-primer. Generally, the RNAse H activity is supplied by a retroviral reverse transcriptase provided for amplification.

Chromosomal translocations and their transcription products have been detected using methods that include nucleic acid amplification. A PCR-based method to detect cells containing genomic DNA having t(14q32;1 Bq21) chromosomal translocations associated with follicular lymphomas, and especially with minimal residual or relapse disease, by amplifying sequences surrounding a breakpoint cluster region, have been described in U.S. Pat. No. 5,024,934 to Lee. PCR primers and cDNA amplification methods for identifying t(9;11) translocations in a patient's tissue have been described in U.S. Pat. No. 5,633,135 to Croce et al. Methods for detecting carcinoma metastases (one in 10,000 to 100,000 cells) involving PCR amplification of target nucleic acids have been described by Green et al. in European Pat. Publication No. EP 520794.

Similarly, PCR amplification has been used to detect chimeric mRNA associated with ALL (U.S. Pat. No. 5,057,410 to Kawasaki et al.) and RNA transcripts originating from t(8;21) translocation in leukemic cells (U.S. Pat. No. 5,547,838 to Nisson et al.). U.S. Pat. No. 5,057,410 to Kawasaki et at discloses PCR methods to detect chimeric mRNA containing exon—exon junctions. In this method, mRNA extracted from the target cell is reverse transcribed to produce cDNA that is amplified by PCR to make a double-stranded DNA amplification product. This amplification product is then denatured and one of the resulting strands is detected by hybridizing an oligonucleotide probe to the breakpoint junction. Individual probes hybridize to distinct bcr-abl junction species associated with CML and ALL.

Sooknanan at al. (*Experimental Hematol.* 21:1719–1724, 1993) described a method for the detection of bcr abl mRNA characteristic of CML by extracting RNA from FICOLL™- fractionated peripheral blood leukocytes and amplifying a target nucleic acid using an isothermal amplification procedure involving transcription. Serial reactions using four amplification primers (a primary pair in the first reaction and a nested pair in the second reaction) were essential for amplification and detection of bcr-abl mRNA. The amplified nucleic acid produced by this method was of the same sense as the original mRNA and was detected using two different bcr-abl junction probes for detecting two splice junctions. Probes to the breakpoint junctions were used to distinguish normal bcr or abl mRNA from the chimeric bcr-abl mRNA in a patient sample.

PCR-based methods have been used for detecting other translocations associated with cancers or their transcription products. Probes and PCR primers for detecting t(2;13) translocations associated with alveolar rhabdomyosarcoma have been described in U.S. Pat. No. 5,650,278 to Barr et al. A nucleic acid sequence encoding a fusion protein (anaplastic lymphoma kinase or ALK) associated with t(2;5) lymphomas has been disclosed in U.S. Pat. No. 5,529,925 to Morris et al.

There remains a need in the art for a simple, sensitive, and rapid method for the detection of chimeric nucleic acids, particularly chimeric mRNA obtained from biological samples such as blood, marrow, plasma, biopsy tissue, sputum, urine, feces, semen or other body fluids. Preferably, such methods would require a minimum of technical expertise by laboratory personnel and a minimum of specialized laboratory equipment such as centrifuges, thermocycling and electrophoresis equipment, and would use relatively low-cost reagents. Furthermore, there exists a need for an assay for detecting chimeric mRNA that would provide a result capable of interpretation with a minimum of qualification by, for example, reducing the possibilities of false positive and false negative results.

There also exists a need in the art for a simple and rapid method of preparing cytoplasmic nucleic acids, particularly mRNA, for use as a potential target in diagnostic nucleic acid hybridization assays or as a template for nucleic acid amplification. Such simplified preparative methods reduce the need for exhaustive extraction and purification procedures.

A crucial element of methods of detecting RNA (or amplification products made therefrom), particularly mRNA, is the manner of extracting RNA from the cells. Because of the ubiquitous presence of various RNases, extraction methods must preserve the small amounts of target RNA that may be present in a sample. Extraction methods that liberate all nucleic acids (including nuclear nucleic acids) from the target cell, produce samples that contain not only of the target mRNA but also the DNA encoding it which can produce false positive results in many nucleic acid assays.

Previously reported extraction techniques generally involve the use of a chaotropic agent such as guanidinium to lyse the cells. Further processing has typically involved mechanical shearing of the DNA, phenol and chloroform extraction, and ethanol precipitation, or LiCl precipitation of the RNA from the guanidinium. Additional methods specific for mRNA preparation have employed oligo dT (polythymine) immobilized on resins to capture polyadenylated mRNA.

It would be advantageous in diagnostic methods that detect mature cytoplasmic RNA to be able to permeabilize cells to release mature RNA species into the extraction buffer, while not appreciably releasing nuclear material. Thus, DNA and immature nuclear RNA species would not be mixed with the desired target nucleic acid. By precluding initial mixing of desired RNA species and contaminants that contain the same or complementary sequences and/or increase viscosity, additional steps to eliminate iv chromosomal DNA and false positive results may be avoided. A rapid, simple lysis method that will liberate cytoplasmic RNA species while not significantly releasing pre-mRNA or DNA, and that does not require a high level of specialized skill or training is particularly desirable for use in commercial assays and kits. There exists a need for a rapid, easy lysis method that yields RNA suitable for qualitative and/or quantitative nucleic acid amplification or direct detection of specific nucleic acids.

SUMMARY OF THE INVENTION

The present invention is directed to assay methods for the quantification and/or identification of fusion nucleic acids, particularly chimeric mRNA species, in a biological sample.

According to one aspect of the invention, there is provided a method for detecting a fusion nucleic acid including the steps of providing a sample containing a first single-stranded fusion nucleic acid comprising a splice junction and then contacting under nucleic acid amplification conditions the first single-stranded fusion nucleic acid, a first primer capable of hybridizing to the fusion nucleic acid at a first primer binding site located 3' to the splice junction site, and at least one nucleic acid polymerase activity. Next, the method includes amplifying the fusion nucleic acid in a nucleic acid amplification reaction using the first primer to produce a plurality of second nucleic acid strands complementary to at least a portion of the first single-stranded fusion nucleic acid that contains the splice junction site. Each of the second nucleic acid strands includes a complementary splice junction site, a first probe binding site located 3' to and not overlapping the complementary splice junction site, and a second probe binding site located 5' to and not overlapping the complementary splice junction site, wherein the second probe binding site overlaps or is located 3' to sequence complementary to the first primer binding site. Next, the method includes hybridizing the second nucleic acid strands with an oligonucleotide probe under hybridization conditions that permit hybridization of the probe to the first or the second probe binding site, thereby forming a probe:target hybrid, and detecting the probe:target hybrid as an indication of the presence of the fusion nucleic acid in the sample. In one embodiment of the method, the first single-stranded fusion nucleic acid is an mRNA, the first primer is a promoter-primer, the polymerase activity includes an RNA polymerase activity, and the oligonucleotide probe is of the same sense as the mRNA and is capable of binding to the first probe binding site. In another embodiment, the first single-stranded fusion nucleic acid is a mRNA, the second nucleic acid strands are complementary RNA, and the method also includes contacting the second nucleic acid strand with a second primer or promoter-primer capable of hybridizing to a second primer binding site located 3' to both the complementary splice junction and the first probe binding site, and using in the amplifying step an RNA polymerase activity, a DNA-directed DNA polymerase activity and an RNA-directed DNA polymerase activity. In one embodiment, the oligonucleotide probe is capable of binding to the second probe binding site and incapable of forming a stable hybridization complex with the first single-stranded fusion nucleic acid. In a preferred embodiment, the fusion nucleic acid is a bcr-abl fusion mRNA and the oligonucleotide probe is capable of binding to a bcr-derived nucleotide base sequence in the second nucleic acid strands. The method described above may also include a step of preparing the sample containing the fusion nucleic acid by contacting a biological sample containing the fusion nucleic acid with a solution that includes a buffer, about 150 mM to about 1 M of a soluble salt, about 0.5% to about 1.5% (v/v/) of a non-ionic detergent, and a solid support to which is joined an immobilized oligonucleotide comprising a nucleotide base sequence capable of forming, directly or indirectly, a stable hybridization complex with an RNA under conditions permitting the formation of the stable hybridization complex, and then separating the hybridization complex joined to the solid support from unhybridized sample components. In a preferred embodiment, the fusion nucleic acid is mRNA, which more preferably is isolated using an immobilized oligonucleotide that includes a poly-T sequence.

Another aspect of the invention is a method of detecting a fusion mRNA transcript produced as a result of a chromosomal translocation. This method includes the steps of providing a sample containing a fusion mRNA transcript comprising a splice junction, and contacting under nucleic acid amplification conditions the fusion mRNA transcript, a first primer capable of hybridizing to the fusion mRNA transcript at a first primer binding site derived from a first chromosomal region and located 3' to the splice junction site, and at least one enzyme having nucleic acid polymerase activity. Then, the method includes the step of amplifying the fusion mRNA transcript in a nucleic acid amplification reaction that uses the first primer to produce a plurality of second nucleic acid strands complementary to at least a portion of the fusion mRNA transcript containing the splice junction site. Each of the second nucleic acid strands includes a complementary splice junction site, a first probe binding site located 3' to and not overlapping the complementary splice junction site, wherein the first probe binding site is derived from a second chromosomal region, and a second probe binding site located 5' to and not overlapping the complementary splice junction site, wherein the second probe binding site is derived from a third chromosomal region and overlaps or is located 3' to sequence complementary to the first primer binding site. The next step in the method is hybridizing the second nucleic acid strands with an oligonucleotide probe capable of hybridizing to the second nucleic acid strands at the first or the second probe binding site but incapable of hybridizing to the fusion transcript, thereby forming a hybridization complex of the probe and the second nucleic acid strand, followed by detecting the hybridization complex as an indication of the presence of the fusion transcript in the sample. In one embodiment, the amplifying step uses only a first primer that is a promoter primer and the enzyme has an RNA polymerase activity, and the hybridizing step uses an oligonucleotide probe capable of hybridizing to the second nucleic acid at the first probe binding site. In another embodiment, the first probe binding site and the second probe binding site are derived from different locations on the same chromosome in a eukaryotic cell, and the fusion mRNA transcript detected results from an intrachromosomal translocation. In an alternative embodiment, the first probe binding site is derived from a different chromosome than the chromosome from which the second probe binding site is derived, and the fusion mRNA transcript detected results from a translocation involving different chromosomes. In preferred embodiments, the fusion mRNA transcript results from a translocation of human chromosomes selected from the group consisting of t(1;19), t(2;5), t(2;13), t(4;11), t(6;9), t(8;21), t(9;11), t(9;22),t(11;14), t(11;19), t(11;22),t(12;21), t(14;18) and t(15;17)translocations. More preferably, the fusion mRNA transcript results from a human t(9;22) translocation and the oligonucleotide probe includes a bcr-derived sequence or an abl-derived sequence. Preferred oligonucleotides suitable for use in this method include one or more having a sequence selected from the group consisting of SEQ ID NO:1 to SEQ ID NO:23, SEQ ID NO:26 and SEQ ID NO:27. In one embodiment, the amplifying step uses an RNA polymerase activity, a DNA-directed DNA polymerase activity, and an RNA-directed DNA polymerase activity, and further uses a second primer or promoter primer capable of hybridizing under amplification conditions to a nucleotide sequence of a complementary RNA produced during the amplifying step. In a preferred-embodiment, the RNA-directed DNA polymerase activity and DNA-directed DNA polymerase activity are supplied by a reverse transcriptase. In another embodiment, the method may also include the steps of amplifying an internal control transcript in the sample by using the first primer and then hybridizing a second oligonucleotide probe capable of hybridizing to the complement of the internal control transcript but incapable of hybridizing to the complement of the fusion mRNA transcript thereby forming in internal control hybridization complex, and detecting the presence of the internal control hybridization complex in the sample, thereby providing an internal standard.

Another aspect of the invention is a method of preparing a sample containing RNA suitable for amplification. This method includes the steps of providing a biological sample containing unpurified RNA, mixing the biological sample with a solution that includes a buffer at a pH of about 6.5 to about 8.5, at least about 150 mM of a soluble salt, an effective amount of a non-ionic detergent sufficient to release RNA from the biological sample without causing viscosity due to release of chromosomal DNA, and a solid support to which is joined an immobilized oligonucleotide comprising a nucleotide base sequence capable of forming a stable immobilized oligonucleotide:RNA hybridization complex, then separating the hybridization complex joined to the solid support from unhybridized sample components; and washing the hybridization complex joined to the solid support with a solution having sufficient salt concentration to maintain the hybridization complex. In a preferred embodiment, the biological sample is uncoagulated blood, plasma or bone marrow. In one embodiment, the effective amount of the non-ionic detergent is between about 0.5% to about 1.5% (v/v) of a non-ionic detergent, which preferably is an octylphenoxy polyethoxyethanol, a polyoxyethylene (20) sorbitan mono-oleate or Nonidet P-40. Another embodiment mixes a volume of cells to a volume of the solution at a ratio of about 1:1 to about 1:3. Preferably, the mixing step uses a solid support that contains magnetic or paramagnetic particles to which is joined the immobilized oligonucleotide, and the separating step applys a magnetic field to the particles. In another embodiment, the separating step uses centrifugation to separate the hybridization complex joined to the solid support from unhybridized sample components. In preferred embodiments, the washing step includes serial washings of the hybridization complex joined to the solid support using a solution that includes a buffer, a chelating agent, about 150 mM NaCl and about 0.1% (w/v) of sodium dodecyl sulfate. More preferably, about three serial washing steps are used.

The invention is more fully described in the detailed description that follows, with preferred embodiments illustrated in the figures and examples.

BRIEF DESCRIPTION OF THE FIGURES

FIG. 2 shows the 5' to 3' DNA base sequence (SEQ ID NO:24) of the region surrounding the bcr-abl splice junction, as shown schematically in FIG. 1A, whew the underlined region (residues 1 to 126) represents to bcr b2 sequence containing the sequence complementary to a primer binding site (bolded residues 65 to 88, SEQ ID NO:6) and the sequence complementary to the b2 probe binding site (bolded and italicized residues 89 to 113, SEQ ID NO:9); the double undefined region (residues 127 to 201) represents the bcr b3 sequence; the splice junction occurs between bases 201 and 202 and the remaining sequence is the A2 region of abl containing the abl primer binding site (bolded, SEQ ID NO:22).

FIG. 3 shows the 5' to 3' DNA base sequence (SEQ ID NO:25) of the region surrounding a potential splice junction in a normal abl transcript where: residues 1 to 151 are abl 1b exon sequence containing a region complementary to an abl primer binding site (residues 84–103, bolded, SEQ ID NO:13); the double-underlined region (residues 102 to 119, SEQ ID NO:26) is the complement of an abl-specific probe binding site flanking the splice junction of abl b1 and abl b2; the underlined region (residues 142 to 165. SEQ ID NO:16) is the complement of second probe binding site that overlaps potential splice junctions; and residues 175 to 201 (bolded, SEQ ID NO:22) are normal abl sequence containing another primer binding site.

DETAILED DESCRIPTION OF THE INVENTION

Figure 1A:
FIG. 1A is a schematic depiction of detection of a fusion transcript produced from a translocation between the bcr b3 region and the abl gene by using a T7 abl promoter primer ("T7-abl primer") of the opposite sense to the target nucleic acid and a primer that is substantially identical to a sequence in the bcr b2 region ("CML-1") for amplification and a probe that is also substantially identical to a sequence within bcr b2 ("b2 probe"). The dark portion of the bar to the left of the vertical line represents the bar b2 sequence, the dark portion to the right of the vertical line represents the bcr b3 sequence, and the light portion represents abl sequence.

The present invention includes methods of preparing RNA samples derived from biological samples, such as body fluids, tissue or eukaryotic cells. This is a relatively simple method of RNA preparation that provides RNA suitable for analysis and detection of mRNA species that occur in relatively low abundance in biological samples. The present invention also includes a method for detecting chimeric RNA species, particularly mRNA species that occur in relatively low abundance in RNA samples prepared from biological sources. These methods are useful for medical diagnoses and clinical monitoring of a patient's response to therapy where a disease or medical condition is associated with a particular type and/or level of mRNA present in a biological sample. These methods are useful in both the human medical and veterinary fields.

In addition to the definitions provided elsewhere in the specification, the following terms have the following meanings unless indicated otherwise. In addition, other scientific and technical terms used herein have the same meaning as commonly understood by those skilled in the relevant art. General definitions of many of the terms used herein are provided in *Dictionary of Microbiology and Molecular Biology* 2nd ed. (Singleton et al., 1994, John Wiley & Sons, New York, N.Y.), *The Harper Collins Dictionary of Biology* (Hale & Marham, 1991, Harper Perennial, New York, N.Y.), and *Dorland's Illustrated Medical Dictionary*, 27th ed. (W. A. Dorand, 1988, W. B. Saunders Co., Philadelphia, Pa.).

By "nucleotide sequence" is meant the sequence of nitrogenous bases along a linear information-containing molecule that is able to hydrogen-bond with a DNA or RNA having a complementary base sequence. Thus, the term is not meant to limit such information-containing molecules to polymers of nucleotides but also includes molecules containing one or more nucleotide analog, such as subunits containing a sugar moiety or substitute other than ribose or deoxyribose (for example, 2' halide- or methoxy-substituted pentose sugars) and linkages other than phosphodiester linkages, such as phosphorothioate, methylphosphonate, and peptide linkages.

A hydrogen-bonded nucleic acid duplex contains two complementary nucleic acid strands. These related strands are said to be of opposite "sense", in that the nucleotide sequence of either of two perfectly complementary nucleic acid strands automatically dictates the nucleotide sequence of the other strand, even though the nucleotide sequence of each strand is different that the other. Conventionally, one strand is arbitrarily designated as the (+) strand and the other related strand is designated as the (−) strand.

By "oligonucleotide" is meant a polymeric chain of two or more, generally between about 5 and about 100, chemical subunits, each subunit comprising a nucleotide base moiety, a sugar moiety, and a linking moiety that joins the subunits in a linear spacial configuration. The most common nucleotide base moieties are guanine (G), adenine (A), cytosine (C), thymine (T) and uracil (U), although other rare or modified nucleotide bases able to form hydrogen bonding are well known by those skilled in the art. The most common sugar moieties are ribose and deoxyribose, although 2'-O-methyl ribose, halogenated sugars, and other modified and different sugars are known. The linking group is usually a phosphorus-containing moiety, most commonly a phosphodiester linkage, although other linkages, such as phosphorothioates, methylphosphonates, and non-phosphorus-containing linkages such as peptide-like linkages are known in the art, as are oligonucleotides comprising such linkages ("peptide nucleic acid" or PNA). PNA are intended to fall within the definition of an oligonucleotide herein. Likewise, nucleotide base moieties may be modified, such as by the addition of propyne groups, so long as the modified base moiety retains the ability to form a non-covalent association with G, A, C, T or U and an oligonucleotide comprising one or more the modified nucleotide base moiety is not sterically prevented from hybridizing with a single-stranded nucleic acid. An oligonucleotide has a sequence of nucleotide base moieties that provides information permitting the oligonucleotide to hybridize with a complementary nucleic acid strand.

By "nucleic acid amplification conditions" is meant environmental conditions including salt concentration, temperature, the presence or absence of temperature cycling, the presence of a nucleic acid polymerase, nucleoside triphosphates, and cofactors that are sufficient to permit the amplification of a target nucleic acid using a given nucleic acid amplification method.

By "primer" is meant an oligonucleotide able to bind to a region of a target nucleic acid and promote nucleic acid amplification of the target nucleic acid. In most cases a primer will have a free 3' end that can be extended by a nucleic acid polymerase. A promoter primer is an oligonucleotide with a promoter sequence located to the 5' side of the target-binding region. Under certain circumstances the 3' end of a promoter-primer, or a subpopulation of such promoter-primers, may be modified to block or reduce primer extension.

By "target sequence" is meant the nucleotide base sequence of a nucleic acid strand, at least a portion of which is able to be detected using a labeled oligonucleotide probe, that is bounded on its 3' side by a primer-binding site, and the exactly complementary RNA or DNA base sequence.

By "RNA equivalents" is meant an oligonucleotide or ribonucleic acid having the same nucleotide base sequence as a deoxyribonucleic acid or another oligonucleotide, except that uracil is substituted in the former when thymine is present in the later.

A "solid support" is a material, essentially insoluble under the given solvent and temperature conditions, comprising free chemical groups available for joining an oligonucleotide or nucleic acid. In a particularly preferred embodiment, the solid support is covalently coupled to an oligonucleotide designed to directly or indirectly bind a target nucleic acid. When the target nucleic acid is an mRNA, the oligonucleotide preferably comprises a polythymine nucleotide base sequence. The solid support is also preferably a particle such as a bead or sphere in the micron or submicron size range. The solid support is made of materials that may include one or more of the following: silica, polyacrylate, polyacrylamide, a metal, polystyrene, latex, nitrocellulose, polypropylene, and nylon. Preferably, the solid support is able to be affected by a magnetic field. In such a case, the solid support may have a magnetite core.

By "nucleotide sequence" is meant the sequence of nitrogenous bases along a linear information-containing molecule that is able to hydrogen-bond with a DNA or RNA having a complementary base sequence. Thus, the term is not meant to limit such information-containing molecules to polymers of nucleotides; rather the term includes molecules containing one or more nucleotide analog, such as subunits containing a sugar moiety or substitute other than ribose or deoxyrbose (e.g., 2' halide- or methoxy-substituted pentose sugars) and linkages other than phosphodiester linkages, such as phosphorothioate, methylphosphonate, and peptide linkages.

By "splice junction probe" or "breakpoint junction probe" is meant that the indicated probe is sufficiently complementary to hybridize to regions comprising both the 5' and 3' sides of a splice point or of a chimeric nucleic acid, respectively.

By "splice junction site" is meant the position, in the nucleotide base sequence of a nucleic acid or oligonucleotide (or its complementary strand), at which the base sequences to the 5' of the splice site on a single strand of the nucleic acid are derived from a first nucleic acid region and the base sequences to the 3' side of the splice site (with reference to the same strand) are derived from a second nucleic acid region, and wherein the first and second region are normally not contiguous.

By a "fusion" or "chimeric" nucleic acid is meant a nucleic acid or oligonucleotide that contains contiguous or adjacent nucleotide base sequences derived from a first and second nucleic acid region, wherein the first and second nucleic acid region are not normally adjacent or contiguous in the DNA of normal cells. Normally, the chimeric nucleic acid is found in nucleic acids of abnormal cells, while the first and second nucleotide base sequence regions are not normally present in normal cells of the same type.

The present invention includes a simplified and rapid procedure for preparation of RNA from a biological sample, particularly from the cytoplasm of eukaryotic cells, which is suitable for use in an amplification and detection assay. This method may also be used to prepare viral RNA from a biological sample such as plasma. This procedure does not require extensive extraction, shearing of chromosomal DNA to reduce viscosity, or the use of potentially harmful reagents (e.g., phenol or chloroform) to prepare RNA. Moreover, by minimizing the number of steps in sample preparation, there is less opportunity for variability and sample loss during the procedure. Thus, this aspect of the invention is useful in providing increased reliably and reproducibly in RNA preparation, particularly for assays that detect low abundance mRNA species.

The invention also includes a method of detecting or quantifying RNA species, particularly chimeric mRNA species. This method includes an initial step of contacting: (1) a first single-stranded fusion nucleic acid that includes a splice junction site, (2) a first primer or promoter-primer capable of hybridizing to the fusion nucleic acid at a primer binding site located 3' to the splice junction site, and (3) at least one nucleic acid polymerase activity, under nucleic acid amplification conditions. Then, the method proceeds to amplifying the fusion nucleic acid in a nucleic acid amplification reaction, thereby producing multiple second nucleic acid strands, each of which includes a region complementary to a region of the initial single-stranded fusion nucleic acid that includes the splice junction site, a first probe binding site located 3' to and not overlapping the splice junction site, and a second probe binding site located 5' to and not overlapping the splice junction site. The second probe binding site can overlap or be located to the 3' side of the first primer binding site. Then, the method includes hybridizing the complementary second nucleic acid strand under hybridization conditions with an oligonucleotide probe capable of hybridizing to the first or the second probe binding site, thereby forming a probe:target hybrid (i.e., a hybridization complex formed by complementary base pairing between the probe's base sequence and the target's base sequence). The probe:target hybrid is detected as an indication of the presence of the fusion nucleic acid in the sample from which single-stranded fusion nucleic acid was obtained. In this method, if the fusion nucleic acid is RNA, the oligonucleotide probe is of the same sense as the single-stranded fusion nucleic acid. If only one primer (or promoter-primer) is used in the amplifying step, then the probe is targeted to the first probe binding site.

It is important to note that this method does not use nested primers and does not require use of serial amplification reactions. Preferably, the method uses a transcription-mediated amplification system that was previously described in detail in U.S. Pat. Nos. 5,480,784 and 5,399,491 to Kacian & Fultz, and U.S. Pat. No. 5,554,516 to Kacian et al., hereby incorporated by reference herein. In one embodiment of the present method, two oligonucleotides are used in the amplification procedure: one promoter primer of opposite sense than the fusion RNA to be detected and one primer of the same sense as the fusion RNA in a location 5' to both the binding site of the promoter primer and the splice junction.

As used herein, a "promoter-primer" is an oligonucleotide that contains at least two distinct nucleotide base sequences. The first sequence is the primer sequence, and renders the promoter-primer capable of hybridizing to a binding site of the fusion RNA at a location 3' to the splice junction. The second sequence is the promoter sequence, located 5' to the primer sequence and capable, when made double-stranded, of providing a preferred binding site for an RNA polymerase to begin transcription of the nucleotide base sequence to which the promoter primer is hybridized (i.e., RNA synthesis using the chimeric RNA as a template). An example of a promoter-primer is SEQ ID NO:1 in which residues 1 to 27 provide a T7 promoter sequence, when made double stranded, and residues 28 to 54 provide a primer sequence capable of binding to a complementary nucleic acid base sequence.

In another embodiment, the assay uses a single amplification oligonucleotide that is a promoter-primer. When a single promoter-primer is employed with no primer of the opposite sense, the chimeric RNA is detected using a probe of the same sense as the chimeric RNA and capable of hybridizing with a nucleotide base sequence region located 3' to the splice junction on the amplified complementary nucleic acid. In this manner, only the amplified chimeric RNA is detected. Nucleic acid amplification methods employing a single promoter-primer have been previously described in U.S. Pat. No. 5,554,516 to Kacian et al., the details of which are hereby incorporated by reference.

Preferably, the primers (including the promoter-primer and the probe as described above) are directed to regions that are normally discontinuous within the chromosomal DNA. For example, in a preferred embodiment of the method the regions comprise nucleotide base sequences that are normally present on different chromosomes. Likewise, for detecting nucleic adds that comprise regions derived from both viral (i.e., provirus) and eukaryotic nucleic acids, the sequences contained in these individual regions are normally not continuous. Additionally, the regions to be detected maybe those that are normally present on separate pans of the same chromosome, but are so widely separated that they would not be co-amplified by common amplification methods in the absence of a splicing or intrachromosomal translocation event.

In an embodiment in which two primers are used, the detection probe may be directed to a nucleotide base sequence located on either side of the splice junction site. In this aspect of the present invention, the probe must be of the same sense as the chimeric RNA. The amplified opposite sense nucleic acids are detected, thereby permitting discrimination of "normal" mRNA (which is not amplified) from spliced RNA (which has been amplified). Furthermore, because the probe is not directed to the splice junction, but instead to a flanking sequence located outside the breakpoint or splice region, a single probe can detect multiple spliced forms.

By "flanking" the site of translocation is meant that the oligonucleotide binding sites are located at positions on either side of the splice junction or the breakpoint cluster region. In many diseases and conditions associated with chromosomal translocations, there may be multiple possible species of chimeri RNA. In each chimeric RNA, a known splice junction has a particular nucleotide sequence to which probes may be designed, but this type of detection would require inclusion of splice junction probes directed not only to common chimeric RNA species, but also to rarer ones.

Because many characterized translocations have breakpoints clustered in discrete, known regions that are associated with the given disease or condition. Therefore, to detect a translocation as a marker for a given condition or disease, is not necessary to detect or even have characterized each species of chimeric RNA. Instead, it is only necessary to detect whether an RNA associated with a translocation event has been produced by the target cell and amplified according to the current method.

In a preferred aspect of the present invention, the ability of the target mRNA to be amplified indicates that the translocation has occurred. In other aspects, such as in the amplification method employing a single promoter-primer, both normal and spliced transcripts will be amplified, but the probe will not hybridize to the nucleic acids amplified from the normal transcript. In either case, detection of the amplified RNA may use any of a variety of known methods such as gel electrophoresis, increase in light absorption, hyperchromatic shift, or use of a detectable oligonucleotide probe, preferably a labeled oligonucleotide probe. Labels suitable for use include enzymes, enzyme substrates, fluorescent, luminescent, chemiluminescent and electrochemiluminescent molecules, radionuclides, and fluorescent atoms, preferably a fluorescent or chemiluminescent label, and more preferably an acridinium ester.

The probes may be targeted to any region of the amplified nucleic acid, so long as the probe is capable of hybridizing to the amplified nucleic acid. In a preferred embodiment, the probe detects sequences outside of the splice junction (i.e., flanking probes), thus broadening the number of differently spliced oligonucleotides that may be detected using this method.

Figure 1B:
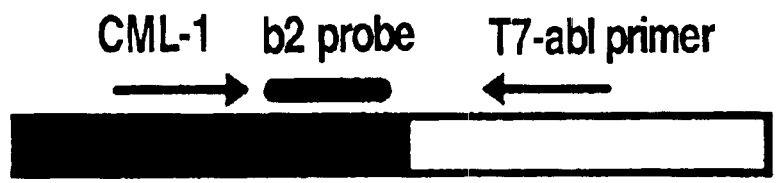
FIG. 1B is a schematic depiction of detection of a fusion transcript produced from a translocation between the bcr b2 region and the abl-1 gene using the same combination of primers and probe are used in FIG. 1A; the dark portion of the bar represents the bcr b2 sequence and the light portion represents abl sequence.
Figure 1C:
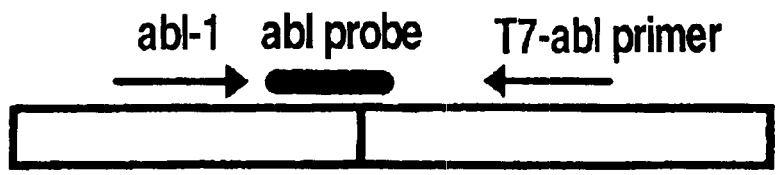
FIG. 1C is a schematic depiction of detection of the normal abl mRNA using a T7 abl promoter primer ("T7-abl primer") of the opposite sense to the target nucleic acid and an "abl-1" primer of the same sense as the target nucleic acid, and an "abl probe" that is substantially identical to an abl target sequence, here shown at a location overlapping a potential breakpoint junction in the abl sequence (shown as a vertical line in the bar).

An example of such an assay is schematically illustrated in FIGS. 1A to 1C, which show two fusion target nucleic acids (FIGS. 1A and 1B) and a normal target nucleic acid (FIG. 1C) which is included as an optional internal control for the amplification and detection method. Referring to FIGS. 1A and 1B, the fusion target nucleic acids (represented by the darkened and open bars) can be amplified using primers and the amplicons detected with a probe directed to a nucleotide base sequence flanking the splice junction (the junction of the darkened and open sections of the bars) to indicate the presence of the spliced nucleic acid in the biological sample. This assay format is capable of detecting any of a family of potential spliced nucleic acids, because the probe does not recognize the spliced junction. FIG. 1C shows an internal control (or "non-target" nucleic acid) in such an assay where a normal target nucleic acid is also amplified and detected in the sample. The internal control indicates that the nucleic acids in the sample were capable of being amplified and detected by a probe (i.e., the absence of contaminants that would inhibit one or both of these steps in the assay).

As illustrated in FIGS. 1A and 1B, amplification of target nucleic acids need not be confined to a single size or category of splicing event. In FIGS. 1A and 1B the target nucleic acids are fusion products of two different bcr-abl translocations, one pining the bcr b3 with abl (FIG. 1A) and one joining the bcr b2 with abl (FIG. 1B). The target nucleic acids are amplified using primers directed to sites on normally non-proximal portions of the nucleic acid, such as sites normally contained on different chromosomes (e.g., the bcr site located on human chromosome 22 that is recognized by the "CML-1" primer, and the abl site located on human chromosome 9 that is recognized by the "T7-abl primer").

As shown in FIGS. 1A and 1B, amplification of target nucleic acids uses one primer specific for one of the nucleic acids involved in the chimeric splicing event (e.g., the "T7-abl primer" specific for abl sequence) and a second primer specific to the other nucleic acid involved in the chimeric splicing event (e.g., the "CML-1" primer specific for bcr sequence). The amplified target sequences are detected using a probe specific for one of the two sequences (i.e., the "b2 probe" specific for the bcr partner in the splicing events shown in FIGS. 1A and 1B). This combination of primers and probe is capable of detecting more than one chimeric splicing event because the same primers are capable of amplifying different sized products that are the result of different splicing events (e.g., compare the relatively long amplified product obtained using the CML-1 and T7-abl primers with the fusion product of FIG. 1A and the relatively short amplified product obtained using the same primers with the fusion product of FIG. 1B), all of which are detectable with the same probe (i.e., the b2 probe). Thus, the fusion transcripts resulting from any of a variety of abnormal splicing events are detectable independent of the particular sequences of the breakpoint junctions.

The assay may optionally include amplification and detection of an internal control (non-target) nucleic acid using one primer that is also used for amplification of the target nucleic acids (e.g., the T7-abl primer in FIGS. 1A to 1C). A second primer used for internal control amplification must be different from the second primer used in amplifying target sequences and is directed to a normally proximate region on the other side of the region that may contain one or more potential splice junctions (e.g., the abl-1 primer as shown in FIG. 1C). Preferably, this second primer is capable of amplifying the internal control nucleic acids at a site dose to the breakpoint junction region to eliminate the possibility that an abnormal splicing event is mistaken for normal nucleic acids. That is, because of the second primer's proximity to the potential splice junction region, the amplification product of the internal control nucleic acid will include a sequence for probe hybridization that will often be eliminated by abnormal splicing events. As illustrated in FIG. 1C, amplification of "non-target" normal abl nucleic acid uses primers for sequences that would normally be contiguous on non-fusion nucleic acid (e.g., the "abl-1" primer and the "T7-abl primer"). A second probe is needed for detection of the amplified internal control nucleic acids (e.g., the "abl probe" in FIG. 1C). This probe is unique to the internal control sequence on the same side of the potential splice junction region as the non-target-specific primer.

The relationships of these sequence regions are shown in greater detail in FIGS. 2 and 3. FIG. 2 shows the 5" to 3" DNA sequence (SEQ ID NO:24) of the region surrounding a bcr-abl splice junction, as shown schematically in FIG. 1A, where the underlined region (residues 1 to 126) represents the bcr b2 sequence containing the sequence complementary to the CML-1 primer binding site (bolded residues 65 to 88; SEQ ID NO:5) and the sequence complementary to the b2 probe binding site (bolded and italicized residues 89 to 113; SEQ ID NO:9). The double underlined region (residues 127 to 201) represents bcr b3 sequence containing a splice junction between residues 201 and 202. From residue 202 to the end of the sequence shown in FIG. 2 is the abl A2 region that contains the primer binding site (bolded; SEQ ID NO:22) for the T7-abl primer of FIGS. 1A to 1C.

FIG. 3 shows the 5' to 3' DNA sequence (SEQ ID NO:25) surrounding a potential splice junction region in a normal abl DNA. Residues 1 to 151 are abl 1b exon sequence and contain a region complementary to the binding site (bolded residues 84 to 103; SEQ ID NO:13) of the abl-1 primer of FIG. 1C. The double-underlined region (residues 102 to 119; SEQ ID NO:26) are complementary to a probe binding site that flanks the splice junction region. The underlined region (residues 142 to 165; SEQ ID NO:16) includes the potential splice junctions, and is the complement of a probe binding site for the abl probe of FIG. 1C. Residues 152 to 299 are normal abl sequence containing a primer binding site (bolded residues 175 to 201; SEQ ID NO:22) for the T7-abl primer of FIGS. 1A to 1C.

The preferred amplification method used in the present invention produces an amplified nucleic acid ("amplicon") that is an RNA, and even more preferably produces predominantly amplified RNA that is complementary to the target sequence (i.e., of the opposite sense as the target sequence). By "predominantly" is meant at least 50% of the product is complementary RNA, and preferably more than 55% is complementary RNA. Thus, if the target is mRNA, arbitrarily designated (+) sense strands, then the amplification products are preferably (−) sense strands. Using transcription-associated amplification methods as described previously in U.S. Pat. Nos. 5,480,784 and 5,399,491, the promoter-primer is of the (−) sense and the template target nucleic acid is of the (+) sense, a producing amplicons that are of the (−) sense. Although the probe may be any sequence capable of binding to amplification products, preferably the probe is of the (+) sense for hybridizing to (−) sense amplification products. If a first primer is used in common for amplification of both target and internal control nucleic acids, the same relationship of primers, amplification products and probes is also used for control nucleic acid amplification and detection.

These methods are useful for detecting any of a variety of known genetic or physiologic events that result in spliced or otherwise rearranged nucleic acids. These methods are particularly useful for detecting the presence of fusion transcripts or chimeric transcripts that result from genetic translocations, most particularly those associated with pathological conditions or diseases. These methods are suitable for detecting in a biological sample a variety of known translocations that are associated with cancers, particularly forms of leukemia such as CML and ALL.

The methods of the present invention are suitable for detecting any of a variety of known translocations that occurs in humans, requiring only the design of primers and probes for known sequences involved in the translocations (reviewed in Mitelman et al., *Cytogenet. Cell Genet.* 55:358–386, 1990). Detectable translocations include, but not limited to, t(9;22), t(4;11), particularly t(4;11)(q21;q23), t(9;11), particularly t(9;11)(p22;q23), t(11;19), particularly t(11;19)(q23;p13), t(8;21), t(1;19), particularly in pre-B cells, t(11;14),t(2;5), particularly t(2;5)(p23;q35), t(11;22), particularly t(11;22)(q24;q12), t(15;17), t(6;9), t(14;18), t(12;21) and t(2;13) translocations. Sequences suitable as targets for detection of these translocations are included in previously published references, all of which are hereby incorporated by reference (Bakhshi et al., *Cell* 41:899–906, 1985; Bakhshi et al., *Proc. Natl. Acad. Sci. USA* 84:2396–2400, 1987; Barr et al., *Genomics* 11:941, 1991; Chen et al., *Blood* 78:2498–2504,1991; Cleary et al., *Proc. Natl. Acad. Sci. USA* 82:7439–7443, 1985; Cleary et al., *Cell* 47:19–28, 1986; Crescenzi et al., *Proc. Natl. Acad. Sci. USA* 85: 4869–4873, 1988; Domer et al., *Proc. Natl. Acad. Sci. USA* 90:7884–7888, 1993; Dragon-Durey et al., *Leukemia* 12(7): 1159–1162,1998; Groffen et al., *Cell* 36:93–99, 1984; Gu et al., *Cancer Res.* 54:2327–2330, 1994; Hermans et al., *Cell* 51:33–40, 1987; Kakizuka et al., *Cell* 66:663–674, 1991; Kamps et al., *Cell* 60:547–555, 1990; Kawasaki et al., *Proc. Natl. Acad. Sci. USA* 85: 5698–5702; LeBeau et al., *Leukemia* 3(12):866–870, 1989; Mellentin of et al., *Science* 246: 379–382,1989; Mitelman et al., *Cytogenet. Cell. Genet.* 55(1–4):358–386, 1990; Nakamura et al., *Proc. Natl. Acad. Sci. USA* 90:4631–4635, 1993; Nourse et al., *Cell* 60: 535–545, 1990; Sacchi et al., *Science* 231:379–382, 1986; Sarris et al., *Leuk. Lymphoma* 29(5–6): 507–514, 1998; Sawyers et al., *Proc. Natl. Acad. Sci. USA* 87:563–567, 1990; Selleri et al., *Proc. Natl. Acad. Sci. USA* 88:887–891, 1991; Shtivelman et al., *Nature* 315:550–554, 1985; Sooknanan et al., *Experimental Hematol.* 21:1719–1724, 1993; Tkachuk et al., *Science* 250:559–562, 1990; Tsujimoto et al., *Science* 224: 1403–1406, 1984; von Lindem et al, *Mol. Cell. Biol.* 12:1687–1697, 1992; Zhao et al, *Am. J. Hum. Genet.* 47:A119, 1980; and Zemin-VanDeroel et al., *Proc. Natl. Acad. Sci. USA* 88:10735–10739, 1991; U.S. Pat. No. 5,057,410 to Kawasaki et al.; U.S. Pat. No. 5,459,251 to Tsujimoto et al.; U.S. Pat. No. 5,538,846 to Meeker; U.S. Pat. Nos. 5,149,628, 5,198,338, 5,202,429 and 5,242,795 to Croce et al.; U.S. Pat. No. 5,547,838 to Nisson et al.). On the basis of known sequences involved in translocations and/or breakpoint junction region sequences, one skilled in the art may readily design and synthesize primers and probes appropriate for practicing the methods of the present invention when that known information is combined with the present disclosure.

Unless described otherwise, the techniques employed or contemplated herein are standard methodologies well known to those of ordinary skill in the art. The examples of embodiments that follow are provided for illustration only.

EXAMPLE 1

Lysis of Biological Samples and Isolation of mRNA

The following procedure was used to isolate mRNA from biological samples. In this example, blood and bone marrow cells were used individually in the lysis and mRNA isolation procedures. The procedure works equally well on other tissues if the cells are separated into individual cells or small clumps of cells using standard mincing, screening and/or proteolysis methods to limit the number of cells in clumps. The lysis procedure comprises contacting a suspension of target cells with a lysing solution containing at least 150 mM of a soluble salt preferably a lithium halide salt (e.g., LiCl), a chelating agent (egg., ethylenediamine tetraacetic acid (EDTA)) and an amount of a non-ionic detergent effective to lyse the cytoplasmic membrane of the cell without substantially releasing the contents of the nucleus. The non-ionic detergent in the lysing solution was generally an octylphenoxy polyethoxyethanol (a TRITON®-type detergent) although other non-ionic detergents (e.g., TWEEN®-type and NP-type detergents) function equivalently. By "effective amount" is meant an amount of a non-ionic detergent sufficient to cause lysis or permeabilization of the cytoplasmic membrane without causing substantial release of nuclear DNA or RNA, generally between about 0.5% (v/v) to about 2.0% (v/v) TRITON® X-102. A preferred lysing solution contained about 1% (v/v) TRITON® X-102.

In a typical procedure, about 250 μl of uncoagulated blood or bone marrow was added to about 750 μl of the lysing solution. The proportions of each of these two components are not critical, and generally about a 1:1 ratio to about a 1:3 ratio of the components is capable of lysing the samples. The lysing solution used most commonly consisted of 50 mM HEPES (pH 7.5), 1 M LiCl, 5 mM EDTA, and 1% TRITON®X-102. By uncoagulated is meant that the blood or bone marrow was treated upon collection with about 2 mM to about 20 mM EDTA, or an effective amount of heparin or similar anticoagulant known in the art. The pH of the buffer may be in a range above and below neutral (pH 7.0), preferably in a range of about pH 6.5 to about pH 8.5, and more preferably about pH 7.5 to facilitate capture of the mRNA by hybridization, such as described in this example below.

Surprisingly, at this stage, the released RNA was stable, and may be stored at room temperature for at least about 2 hours without significant degradation of the RNA even in the absence of additional RNAse inhibitors. None of the HEPES, LiCl, EDTA or TRITON® X-102 components of the lysing solution by themselves was effective in preventing almost-immediate degradation of the RNA. Thus, it was surprising that the combination of these ingredients was effective in inhibiting RNA degradation.

For mRNA isolation, capture particles were added to the above-described lysis mixture. About 30 μl of a suspension of superparamagnetic particles (approximately 300 μg) to which polythymidine (in a range between $dT_{14}$ to $dT_{30}$) was linked at a density of between approximately 1 to 100 pmoles per mg was added to about 1 ml of the lysis mixture. Particles having $dT_{14}$, $dT_{20}$, $dT_{25}$ and $dT_{30}$ have all been used successfully with these procedures. Generally, the particles had attached between about 10 to 100 pmoles of poly-dT per mg, and most commonly the particles had attached about 10 to 50 pmoles of poly dT per mg of particles. The particles were suspended in standard phosphate buffered saline (PBS), pH 7.4, containing 140 mM NaCl for addition to the lysis mixture.

Typically, the particles used were a magnetite core coated with latex or silica, which are commercially available, to which poly-dT oligonucleotides ("tails") were attached. Although it is not crucial that the particles be magnetic or paramagnetic, the magnetic property aids in the recovery of the particles after hybridization of the liberated messenger RNA onto the particles via the poly-dT tails. Those skilled in the art will appreciate that non-magnetic particles with poly-dT may be substituted and separated using standard sedimentation or filtration methods For coupling to the poly-dT, underivatized particles have free groups such as amine, hydroxyl, carboxyl, ester groups or mixtures of these groups. Appropriate particles may be obtained already derivatized with poly-dT tails from a number of suppliers (e.g., Serodyn, Dynal, Novagen). Alternatively, underivatized particles may be purchased (e.g., from Seradyne) and joined to poly-dT oligonucleotides using well-known coupling chemistry (Lund et al., *Nuc. Acids Res.* 16:10861–10880,1988).

The lysis mixture containing the poly-dT particles was gently mixed by vortexing and then incubated at between about 22° C. to 42° C. for about 30 min. The particles were separated from the remainder of the solution by application of a magnetic field to retain the particles and the supernatant is discarded. Those skilled in the art could readily substitute centrifugation for the particle separation step. The separated particles were washed in about 1 ml of a wash solution of 50 mM HEPES (pH 7.5), 5 mM EDTA, 150 mM NaCl and 0.1% (w/v) sodium dodecyl sulfate (SDS) with mixing by vortexing for about 3 to 5 seconds to suspend the beads. The beads were separated from the supernatant as described above, and the supernatant wash was discarded. The washing procedure was repeated twice and the particles were finally suspended in 250 μl of a buffer consisting of 10 mM HEPES (pH 7.5) and 1 mM EDTA. This suspension was either stored at −30° C. for later use or used immediately. Nucleic acids prepared in this manner have been stored frozen for at least two years with no noticeable diminution in the structural or functional integrity of the nucleic acids.

If the isolated RNA is to be used immediately, it may be either released from the capture particles (such as through a standard low salt elution process) or it may be amplified without releasing it from the particles by using an amplification procedure that obviates the need to elute the nucleic acids. For example, by using primers that bind to regions of the isolated nucleic acid that not involved in base pairing with the poly-dT tails or in other interactions with the solid phase matrix that might interfere with primer binding, one may amplify at least a portion of the bound mRNA without releasing it from the particles.

One skilled in the art will recognize that the exact volumes and proportions exemplified above are not critical to the invention. It is important, however, that samples derived from biological tissue (e.g., blood, bone marrow, plasma or cell suspensions) be treated to prevent coagulation. It is also important for cellular samples that the ionic strength of the lysing solution be at least about 150 mM, preferably between about 150 mM to 1 M, to permit lysis of the cell membrane of a target cell without concomitant release of nuclear DNA. At lower ionic strengths, release of nuclear material resulted in contamination of the released cytoplasmic nucleic acids with nuclear nucleic acids such as chromosomal DNA. Although not wishing to be bound to a theory, Applicants believe that at ionic strength of at least about 150 mM, the nuclear membrane remains sufficiently intact to prevent significant release of chromosomal DNA. Contaminating chromosomal DNA increased the viscosity of the mixture which may interfere with a subsequent assay using the cytoplasmic RNA, for example, by cross-reacting and producing false positive reactions, sequestering the RNA and/or primers, and for preventing mixing of reactants. A lysing solution containing lithium salts is preferred for preventing RNA degradation, although other buffers containing soluble salts (e.g., NaCl) and a known RNAse inhibitor are expected to be equally effective in this selective lysis procedure.

Although the above-described sample preparation method illustrates the isolation of cytoplasmic mRNA, those of skill in the art will realize that, in other embodiments the sample preparation method can be used in conjunction with a mediator oligonucleotide, such as those previously described in U.S. Pat. No. 4,751,177 to Stabinsky. Use of such a mediator oligonucleotide permits hybridization in solution of the mediator oligonucleotide to a specific target nucleic acid, thus taking advantage of the favorable in-solution hybridization kinetics, and immobilization of the target nucleic acid using a particle, such as the homopolymer-linked particles described above. Other methods of immobilizing a target nucleic acid that are suitable for use with nucleic acids prepared by the above-described lysis procedure include those previously described in U.S. Pat. Nos. 4,486,539 and 4,563,419 to Ranki et al., EP Pat. Publication No: 159719 by Rabbani et al., EP Pat. Publication No. 128332 by Pergolizzi et al., U.S. Pat. No. 5,476,769 to Soderlund et al., U.S. Pat. No. 5,474,895 to Ishii et al. and EP Pat. Publication No. 444120 by Homes et al.

This lysis method is useful for the preparation of nucleic acids from cells contained in a variety of tissues. For example, cells originating in solid tissue, such as solid tumor tissue, may be minced and treated with trypsin using standard methods to make a cell suspension that is then lysed as described above. Other suitable methods of putting cells into suspension are known in the art. As shown below, cells grown in tissue culture or liquid medium may also be used.

Although mixing the reagents by vortexing is preferred for small-scale usage of the methods, it may be more advantageous on a large scale to use another, less labor-intensive mixing method known in the art. Known methods that provide thorough and vigorous mixing are within the scope of the invention.

The number of washing steps following linking of the target nucleic acids to the particles may be varied. Three washing steps were usually used before amplifying the nucleic acid. Similarly, the particles may be separated from the supernatant by a variety of means such as filtration, precipitation and centrifugation. The beads may have nucleic acid capture probes joined thereto to specifically bind a specific cytoplasmic nucleic acid, as exemplified above using the particle-bound homopolymeric oligonucleotides. Alternatively, although less preferred, the particles (or any solid phase suitable for washing steps as described above) may non-specifically bind the target nucleic acid, as, for example, by polycationic supports as described in U.S. Pat. No. 5,599,667 to Arnold et al.

The washing steps are important, not only for removing contaminating proteins and nucleic acids from the cytoplasmic nucleic acid preparation, but also for removing lithium that has been found to have an inhibitory effect on at least one of the enzymatic activities (RNA directed DNA polymerase, DNA directed DNA polymerase, RNAse H, and RNA polymerase) used in the transcription based nucleic acid amplification method as described previously in U.S. Pat. Nos. 5,480,784 and 5,399,491 to Kacian & Fultz Lithium salts may not be inhibitory to other enzymes, and thus exchanging the cation after lysis may not be necessary if other amplification enzymes are used.

EXAMPLE 2

Amplification of Isolated Nucleic Acid from a Biological Sample and Detection of Amplified Product Fifty microliters of the bead suspension containing nucleic acids isolated from the blood of a CML positive patent as described in Example 1 was added to a tube containing 25 µl of an amplification reagent containing 160 mM Tris-HCl (pH 7.5), 100 mM $MgCl_2$ 70 mM KCl, 20% (w/v) polyvinylpyrrolidone, 16 mM each of the four ribonucleoside triphosphates ATP, GTP, CTP, and UTP, 4 mM each of the four deoxyribonucleoside triphosphates dATP, dGTP, dCTP, and DTTP, 400 nM (15 pmoles) of a promoter primer having the nucleotide base sequence of SEQ ID NO:1 (TAAATTMTACGACTCACTATAGGGAGACTCA GACCCTGAGGCTCAAAGTCAGA), and 400 nM (15 pmoles) of a primer having the nucleotide base sequence of SEQ ID NO:5 (GACCMCTCGTGTGTGAAACTCCA). The tube was incubated at 60° C. for 10 min. Generally, any temperature that is suitable to melt intramolecular base pairing in the target nucleic acid is permissible at this step. Preferably, the incubation temperature is between about 60° C. and 70° C., more preferably between about 65° C. and about 67 C.

Next, the tube was incubated at about 42° C. for 5 min. An enzyme reagent (25 µl containing 2000 units of recombinant MMLV reverse transcriptase, 2000 units recombinant T7 RNA polymerase, 8 mM HEPES (pH 7.5), 50 mM N-acetyl-L-cysteine, 0.04 mM zinc acetate, 80 mM trehalose, 140 mM Tris-HCl (pH 8.0), 70 mM KCl, 1 mM EDTA, 0.01% (w/v) phenol red, 10% (v/v) TRITON® X-102 and 20% (v/v) glycerol) was added to the reaction mixture and the tube was gently mixed and incubated for about 1 hr at 42° C. This amplification method produced amplified RNA of a sense opposite to that of the target RNA.

Amplified RNA was detected using 100 µl of a probe reagent containing 100 mM lithium succinate (pH 4.7), 1.2 M LiCl, 15 mM aldrithiol-2,2% (w/v) lithium lauryl sulfate (LLS), 20 mM EDTA, 20 mM ethylene glyco-bis-(β-amino ethyl ether) N,N,N',N'-tetracetic acid (EGTA), 3% ethanol, and 7.5 nM of a hybridization probe labeled with a chemiluminescent acridinium ester (AE). The synthetic DNA probe specific for bcr b2-sequence detection had the sequence of SEQ ID NO: 9 (GACTGTCCACAG CATTCCGCTGACC) that was linked to the AE label using non-nucleotide linkers and methods previously described in U.S. Pat. No. 5,585,481 to Arnold et al. This detection solution was added to the reaction mix and incubated at 60° C. for 30 min to permit hybridization of the probe to the amplified target.

The probe was detected in a homogeneous assay format, such as the homogeneous protection assay (HPA) described in detail in U.S. Pat. No. 5,283,174, to Arnold et al. Briefly, 300 µl of an alkaline solution containing 600 mM sodium borate (pH 8.5) and 1% (v/v) TRITON® X-100 was added to the mixture described above to hydrolyze the AE label on unbound probe. The AE label on hybridized probe is protected from hydrolysis by Hs association with a double helix, whereas AE label on unhybridized probe is not protected from hydrolysis. Thus, unhybridized probe is preferentially made undetectable. The solution was incubated at 60° C. for 10 min, cooled to room temperature for 5 min and mixed with 200 µl of a solution containing 30 mM hydrogen peroxide and 1 mM nitric acid, followed immediately by addition of 200 µl of a solution containing 1 M NaOH and 2% (w/v) ZWITTERGENT® 3–14. Chemiluminescence was detected using a luminometer (e.g., LEADER® 1, LEADER® 50, LEADER® 450 or LEADER® 450-HC) with the output measured in relative light units ("RLU").

Although the method exemplified herein employs specific detection formats for detecting a nucleic acid probe, those skilled in the art could readily use labels other than AE, such as radioactive labels, fluorescent and other chemiluminescent labels to detect the hybridized probe using standard methods. Likewise, although homogeneous assay systems have certain clear advantages over heterogeneous assays (i.e., those necessitating physical separation to differentiate signal of hybridized probe from signal due to unhybridized probe), the homogeneous detection aspect is not critical to the method.

EXAMPLE 3

Amplification of Isolated Spliced Nucleic Add and Detection of Amplified Product In this assay, a spliced target nucleic acid resulting from a bcr-abl translocation was amplified and detected with a probe directed to a flanking the splice junction to indicate the presence of the fusion product in the biological sample. The general method used for amplification and detection of the fusion product is illustrated in FIGS. 1A to 1C.

The biological sample used was blood cells obtained from patients known to be positive for CML, from which poly-A RNA was isolated using the lysis method substantially as described in Example 1. Amplification of the RNA was conducted substantially as described in Example 2, but using the promoter-primer of SEQ ID NO:1, the primer of SEQ ID NO:5 and 400 nM of an abl-specific DNA primer having the sequence of SEQ ID NO:13 (CAAAGGAGCAGGGA AGAAGG). This abl-specific primer is of the same sense as the target nucleic acid.

Prior to detection, the amplified nucleic acids were divided into two aliquots. The bcr-specific AE-labeled probe of SEQ ID NO:9 was added to the first aliquot for detection substantially as described in Example 2. The bcr-specific AE-labeled probe is functionally the same as the b2 probe described with reference to FIGS. 1A and 1B, and the fusion nucleic acid was detected by measuring RLU as described in Example 2. The bcr-specific AE-labeled probe having the sequence of SEQ ID NO:16

(GTGGMCATGAAGCCCTTCAGCGG) was added to the second aliquot and the mixture was processed for detection of RLU substantially as described in Example 2. This abl-specific probe is capable of hybridizing to the human abl gene spanning a commonly used splice junction region, although a probe directed to 5' of the splice junction region may also be used (see Example 6). Because the primers used in this example were designed to amply each of the fusion target and the normal abl nucleic acids present in the amplification mixture, they co-amplified both types of nucleic acids in the amplification reaction mixture but were separately detectable in the two aliquots of the detection step.

The chemiluminescence of each of the two aliquots was detected substantially as described in Example 2, although the volumes of the reagents was adjusted appropriately to account for the fact that the amplification mixture had been divided (i.e, hall volumes were used).

Alternative procedures may be used to detect each of the target and non-target amplicons. One such alternative procedure makes use of two chemiluminescent labels having different characteristics, such as different wavelengths of light emission, different optimal reaction pH values, or different chemiluminescent reaction kinetics, which characteristics make it possible to detect two different amplicons in the same reaction vessel by employing probes differently labeled with the appropriate label. Such procedures have been previously disclosed in detail in PCT Int'l Pat. Publication No. WO 96/13612 and PCT Int'l Pat. Publication No. WO 91/00511.

EXAMPLE 4

Amplification Using a Single Promoter-Primer and Selective Detection of Amplified Nucleic Acids This example demonstrates nucleic acid amplification using a single promoter-primer capable of hybridizing to the target nucleic acid for the production of amplified nucleic acids of a sense opposite to that of the target. Both normal and fusion nucleic acids were amplified using one primer, but the amplified nucleic acids were detected separately using a bcr probe targeted to a position located to the 5' side (relative to the target nucleic acid) of the breakpoint junction, and one abl probe targeted to an abl sequence that would be missing in the fusion nucleic acid.

For comparison, three different sources of poly-dT magnetic particles were used in this example. Commercially available beads with linked 25-mer poly-dT were purchased (Novagen $dT_{25}$ beads) and two sets of beads were prepared by coupling poly-dT to underivatized particles (purchased from Seradyne) essentially as described in Example 1. One set of beads was coupled to a homopolymeric 14-mer oligonucleotide ("$dT_{14}$ beads"), and a second set of beads was coupled to a homopolymeric 30-mer oligonucleotide ("$dT_{30}$ beads"). Each type of bead was present in a suspension as described above.

Cytoplasmic mRNA was prepared from K562 cells, grown in standard tissue culture to a density of about $5\times10^6$ cells/ml and then treated according to the sample preparation method described in Example 1. Approximately $2\times10^5$ of cells were used for each reaction mixture tested which was then used undiluted or at a 1:10 dilution. In separate reaction mixtures, 60 µl of each washed bead preparation was used per nucleic acid amplification reaction. Control samples had no beads added, to provide a background measurement that was then subtracted from the sample results to which beads had been added. Nucleic acid amplification was performed substantially as described in Example 2 and described more fully in U.S. Pat. No. 5,554,516, to Kacian et al., except that only a single promoter primer of SEQ ID NO:1 (30 pmoles) was used in the amplification reaction; no primers of the same sense as the target nucleic acid were used.

Amplification reactions were allowed to proceed for one hour. Then each sample was divided into two unequal aliquots, one aliquot containing one-third of each amplification reaction being detected with the bcr-specific AE-labeled probe of SEQ ID NO:9, and the other aliquot containing two-thirds of the amplification reaction being detected with the abl specific AE-labeled probe of SEQ ID NO:16. Probe hybridization was performed substantially as described in Example 2. Detection of the hybridized probes was performed substantially as described in Example 2, with the volumes of the detection reagents adjusted proportionately to the volume of sample used. The light emitted by the labels was measured in a LEADER® 50 luminometer in relative light units (RLU) as described previously and the results are shown in Table 1.

TABLE 1

|  | bcr probe | | abl probe | |
| --- | --- | --- | --- | --- |
|  | undiluted | 1:10 dilution | undiluted | 1:10 dilution |
| Novagen beads | 224935 | 95570 | 55807 | 21264 |
| $dT_{14}$ beads | 323646 | 21999 | 109303 | 7725 |
| $dT_{30}$ beads | 12510 | 969 | 13685 | 2607 |

These results indicate that the method of the present invention can be used in an amplification format that uses a single promoter-primer which was designed to hybridize to the complement of the target nucleic acid at a position located 3' to the potential or anticipated splice junction region. Amplification resulted in accumulation of an amplicon (complementary RNA transcript) having the opposite sense as that of the target nucleic acid. The results also indicate that using particles having attached a 14-mer poly-dT oligonucleotide were effective under these assay conditions at capturing mRNA in solution. The commercially-obtained Novagen beads having attached poly-dT were also effective at RNA capture. The amplification reaction using a single promoter-primer may be used to specifically detect the presence of two different nucleic acid transcripts in the same biological sample using different probes: in this case, one detected by the bcr probe, and another detected by the abl probe. Thus, detection of one transcript (e.g., the abl transcript) may serve as an internal control in the sample preparation, amplification and detection steps of the method. Results of other experiments showed no cross reaction between these two probes.

EXAMPLE 5

Amplification and Detection of Normal ab/ Transcripts in Peripheral Blood Cells

Amplification was carried out on nucleic acids isolated from peripheral blood cells and stored before use, substantially as described in Examples 1 and 2. Whole blood treated with EDTA was processed as described in Example 1, and the particles to which cytoplasmic RNA bound were stored as indicated before use. This example shows use of the sample preparation method to prepare normal abl mRNA and of the amplification method to permit the detection of normal abl mRNA. This example also shows that different sources of immobilized dT, having different dT lengths, are effective for target isolation.

The particles used for the isolation of the naturally occurring abl gene product were the same three types as used in Example 4, and the isolation of the cytoplasmic nucleic acids was performed substantially as described in Example 1. The blood specimens were used "undiluted" or at a dilution of 1:10 or 1:100. The particles of each set (60 μg and 6 μg) were used in the transcription-mediated amplification procedure substantially as described in Example 2, using a promoter-primer having the sequence of SEQ ID NO:1 and a second primer having the sequence of SEQ ID NO:13. Following amplification, the amplification products were detected using an abl-specific probe having the sequence of SEQ ID NO:16, using the detection procedures substantially as described in Example 2. Chemiluminescence was measured in RLU as described in Example 2 and the results are shown in Table 2. The negative control (no beads) represents unsubtracted background.

TABLE 2

DETECTION WITH abl PROBE

|  | undiluted | 1:10 dilution | 1:100 dilution | No beads |
| --- | --- | --- | --- | --- |
| 60 μg Novagen beads | 247,314 | 258,311 | 37,434 | 2,181 |
| 6 μg Novagen beads | 19,737 | 10,273 | 2,987 | 1,779 |
| 60 μg dT$_{14}$ beads | 957,6685 | 264,429 | 21,984 | 1,744 |
| 6 μg dT$_{14}$ beads | 67,992 | 14,455 | 2,532 | 1,780 |
| 60 μg dT$_{30}$ beads | 440,204 | 79,873 | 5,135 | 1,548 |
| 6 μg dT$_{30}$ beads | 61,618 | 15,568 | 2,369 | 1,807 |

The data of Table 2 demonstrate the sample preparation techniques described herein as suitable to capture specific nucleic acid species which are then capable of being amplified and detected using a target-specific probe.

EXAMPLE 6

Amplification and Detection of Normal abl Transcripts and Fusion bcr-abl Transcripts in RNA isolated from CML Patients This example demonstrates that bcr-abl transcripts of two different types (bcr b2-abl and bcr b3-abl) can be detected in amplification products of RNA obtained from CML patients using different bcr probes. It further shows that amplification and detection of abl RNA serves as an internal control in the method.

The sources of RNA used in these experiments were: (1) CML patients' RNA obtained from three individuals, and (2) control synthetic RNA transcripts produced by standard in vitro transcription procedures from an abl gene clone (cloned from a patient's RNA using standard cDNA cloning) and a clone containing a bcr b3-abl translocation breakpoint junction (cloned from the K562 cell line). The three CML patients (Patients A, B and C) exhibited different phases of the disease: Patients A and B had active CML symptoms, and Patient C was assayed after receiving a bone marrow transplant and displayed little or no CML symptoms. For each patient, total RNA was isolated from the buffy coat of blood samples using a standard guanidinium isothiocyanate method (Chirgwin, et al., 1979, *Biochem.* 18:5294–5299). The total RNA used for each assay for each patient was about 10 ng, equivalent to about 1,000 cells. The control synthetic RNA were assayed using numbers of copies of the sequence calculated using standard procedures, with the copy number per assay shown in Table 3. The negative controls had no RNA added to the amplification reaction mixtures.

Amplification of the patients' total RNA and the control synthetic RNA transcripts was performed essentially as described in Example 2. Detection of the amplified nucleic acids was done essentially as described in Example 2, but using in each sample: as the bcr b2 probe, an oligonucleotide having SEQ ID NO:9; as the bcr b3 probe, an oligonucleotide having SEQ ID NO:27; and as the abl probe, an oligonucleotide having SEQ ID NO:26. The abl probe is targeted to a region shown in FIG. 3 (double underlined sequence). The assays were performed in triplicate and the average (mean) RLU results are presented in Table 3 ("ND" means "not done").

TABLE 3

| RNA Specimen | abl Probe (SEQ ID NO:26) | bcr b2 Probe (SEQ ID NO:9) | bcr b3 Probe (SEQ ID NO:27) |
| --- | --- | --- | --- |
| Patient A | 928,274 | 6,166,770 | 3,200,051 |
| Patient B | 95,173 | 4,843,570 | 1,547 |
| Patient C | 3,250,592 | 3,304 | ND |
| 20,000 copies abl | 4,676,542 | ND | ND |
| 2,000 copies abl | 1,298,834 | ND | ND |
| 200 copies abl | 130,249 | ND | ND |
| 2,000 copies bcr-abl | ND | 6,012,846 | 3,195,019 |
| 50 copies bcr-abl | ND | 2,756,934 | 729,648 |
| No RNA | 2,305 | 3,344 | 1,591 |

The results of Table 3 show that the bcr b2-specific probe was able to detect as few as 50 copies of bcr b2 (see column 3, data line 8) and detected the presence of bcr b2 in RNA from Patients A and B, but not from Patient C (column 3, data lines 1–3 compared to the "No RNA" control of column 3, data line 9). The results also show that the bcr b3 probe was able to detect as few as 50 copies of bcr b3 (see column 4, data line 8) and detected the presence of bcr b3 in RNA from Patient A, but not in RNA from Patient B. Patient C would not be expected to have bcr b3 because the translocation in that patient had already removed the target of the bcr b2 probe. Table 3 also shows that the internal control, abl, was detected in all three patients, presumably representing normal ab/transcripts (column 2, data lines 1–3). Other results (not shown) have previously confirmed that the bcr b2 and bcr b3 probes do not cross-react with abl amplicons and the abl probe does not cross-react with bcr amplicons.

The foregoing examples illustrate rather than limit the present invention. Other embodiments will be apparent to the skilled artisan and are legally equivalent to the methods defined by the claims that follow.

What is claimed is:

1. A method for detecting a fusion nucleic acid comprising the steps of:
    a) providing a sample containing a first single-stranded fusion nucleic acid comprising a bcr-abl splice junction site;
    b) contacting under nucleic acid amplification conditions: the first single-stranded fusion nucleic acid,
        a first primer which hybridizes to the fusion nucleic acid at a first primer binding site of SEQ ID NO:22 located 3' to the splice junction site, and
        at least one enzyme having nucleic acid polymerase activity;
    c) amplifying the fusion nucleic acid in a single isothermal nucleic acid amplification reaction using the first primer to produce a plurality of second nucleic acid strands complementary to at least a portion of the first single-stranded fusion nucleic acid that contains the bcr-abl splice junction site, wherein each second nucleic acid strand comprises:
    a complementary splice junction site,
    a first probe binding site located 3' to and not overlapping the complementary splice junction site, and a second probe binding site located 5' to and not overlapping the complementary splice junction site;

d) hybridizing the second nucleic acid strands with an oligonucleotide probe under hybridization conditions in which the probe hybridizes to the first or second probe binding site, thereby forming a probe; target hybrid; and e) detecting the probe:target hybrid as an indication of the presence of the fusion nucleic add in the sample.

2. The method of claim 1, wherein the first single-stranded fusion nucleic acid is an mRNA, the first primer is a promoter-primer, the enzyme having nucleic acid polymerase activity comprises an RNA polymerase activity, and the oligonucleotide probe is of the same sense as the mRNA and binds to the first probe binding site.

3. The method of claim 1, wherein the first single-stranded fusion nucleic acid is a mRNA, wherein the second nucleic acid strands are complementary RNA, wherein the amplifying step includes contacting the second nucleic acid stand with a second primer or promoter-primer which hybridizes to a second primer binding site that hybridizes to SEQ ID NO:5 located 3' to both the complementary splice junction site and the first probe binding site, and wherein the amplifying step uses an enzyme having nucleic acid polymerase activity comprising an RNA polymerase activity, and an enzyme having nucleic acid polymerase activity comprising a DNA-directed DNA polymerase activity and an RNA-directed DNA polymerase activity.

4. The method of claim 1, wherein the oligonucleotide probe has a sequence of SEQ ID NO:9 or SEQ ID NO:27.

5. The method of claim 1, wherein step a) includes preparing RNA from the sample containing the fusion nucleic acid by:

contacting a biological sample comprising the fusion nucleic acid with a solution consisting essentially of:
a buffer,
about 150 mM to about 1 M of a soluble salt,
about 0.5% to about 1.5% (v/v) of a non-ionic detergent, and
a solid support to which is joined an immobilized oligonucleotide comprising a nucleotide base sequence which forms, directly or indirectly, a stable hybridization complex with an RNA under conditions permitting the formation of the stable hybridization complex; and
separating the hybridization complex joined to the solid support from unhybridized sample components without extracting the RNA using reagents such as phenol or chloroform.

6. The method of claim 5, wherein the fusion nucleic acid is mRNA.

7. The method of claim 6, wherein the nucleotide base sequence of the immobilized oligonucleotide comprises a poly-T sequence.

8. A method of detecting a fusion mRNA transcript produced as a result of a chromosomal translocation comprising the steps of a) providing a sample containing a fusion mRNA transcription comprising a bcr-abl splice junction site;

b) contacting under isothermal nucleic acid amplification conditions;
the fusion mRNA transcript,
a first primer which hybridizes to a sequence of SEQ ID NO:22, and
at least one enzyme having nucleic acid polymerase activity, c) amplifying the fusion mRNA transcript in a single nucleic acid amplification reaction that uses the first primer to produce a plurality of second nucleic acid strands complementary to at least a portion of the fusion mRNA transcript containing the splice junction site, wherein each second nucleic acid strand comprises:
a complementary splice junction site,
a first probe binding site located 3' to and not overlapping the complementary splice junction site, and
a second probe binding site located 5' to and not overlapping the complementary splice junction site;
wherein the second probe binding site overlaps or is located 3' to sequence complementary to SEQ ID NO:22;

d) hybridizing the second nucleic acid stands with an oligonucleotide probe which hybridizes to the second nucleic acid strands at either the first probe binding site or the second probe binding site but does not hybridize to the fusion mRNA transcript, thereby forming a hybridization complex of the first probe or the second probe and the second nucleic acid strand; and e) detecting the hybridization complex as an indication of the presence of the fusion transcript in the sample.

9. The method of claim 8, wherein the amplifying step uses only a first primer that is a promoter primer of SEQ ID NO:1 and the enzyme has an RNA polymerase activity, and wherein the hybridizing step uses an olignucleotide probe which hybridizes to the second nucleic acid at the first probe binding site.

10. The method of claim 8, wherein the first probe binding site is derived from a different chromosome than the chromosome from which the second probe binding site is derived, and the fusion mRNA transcript detected results from a translocation involving different chromosomes.

11. The method of claim 8, wherein the fusion mRNA transcript results from a human t(9;22) translocation.

12. One or more oligonucleotides suitable for use in the method of claim 11, wherein a nucleotide sequence of the one or more oligonucleotides is selected from the group consisting of SEQ ID NO:1, SEQ ID NO:2, SEQ ID NO:3, SEQ ID NO:4, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:26 and SEQ ID NO:27.

13. The method of claim 8, wherein the amplifying step uses an enzyme having nucleic add polymerase activity comprising an RNA polymerase activity, and an enzyme having nucleic acid polymerase activity comprising a DNA-directed DNA polymerase activity, and an RNA-directed DNA polymerase activity, and further uses a second primer or promoter primer which hybridizes under amplification conditions to a nucleotide sequence of a complementary RNA produced during the amplifying step.

14. The method of claim 13, wherein the enzyme having nucleic acid polymerase activity comprising RNA-directed DNA polymerase activity and DNA-directed DNA polymerase activity is a reverse transcriptase.

15. The method of claim 8, wherein the amplifying step also amplifies an internal control normal abl transcript in the sample by using the first primer to amplify a normal abl sequence in SEQ ID NO:25 and then hybridizing an oligonucleotide probe which hybridizes to the complement of the internal control transcript but does not hybridize to the complement of the fusion mRNA transcript thereby forming in internal control hybridization complex, and wherein the detecting step also detects the presence of the internal control hybridization complex in the sample, thereby providing an internal standard.

16. The method of claim 5, wherein the biological sample is uncoagulated blood, plasma or bone marrow.

17. A method of detecting a fusion mRNA transcript produced as a result of a human bcr-abl translocation comprising the steps of:
   a) providing a sample containing a human fusion mRNA transcript comprising a bcr-abl splice junction site;
   b) contacting under isothermal nucleic acid amplification conditions:
      the fusion mRNA transcript,
      a first primer that binds to a primer binding site of SEQ ID NO:22 which is located in an abl sequence flanking the bcr-abl splice junction site,
      a second primer having a sequence of SEQ ID NO:5, which hybridizes to a bcr sequence flanking the bcr-abl splice junction site,
      at least one enzyme having an RNA-directed DNA polymerase activity, and
      at least one enzyme having an DNA-directed RNA polymerase activity,
   c) amplifying the fusion mRNA transcript in a single nucleic acid amplification reaction that uses
      the first primer,
      the second primer, and
      the DNA-dependent RNA polymerase activity to produce amplified RNA that is complementary to the fusion mRNA transcript comprising the bcr-abl splice junction;
   d) hybridizing the amplified RNA with an oligonucleotide probe which hybridizes to a probe binding site located in an amplified bcr sequence flanking the bcr-abl splice junction, thereby forming a hybridization complex; and
   e) detecting the hybridization complex as an indication of the presence of the fusion mRNA transcript in the sample.

18. The method of claim 17, further comprising:
   in the contacting step, contacting a third primer having a sequence of SEQ ID NO:13 that hybridizes to the complement of a normal abl mRNA transcript,
   in the amplifying step, amplifying a normal abl sequence present in the normal abl mRNA by using the first primer and the third primer,
   in the hybridizing step, hybridizing an oligonucleotide probe that hybridizes to a probe binding site located in an amplified normal abl sequence that is missing in amplified RNA made from the fusion mRNA transcript, and
   in the detecting step, detecting a hybridization complex made up of the probe hybridized to the amplified normal abl sequence that is missing in amplified RNA made from the fusion mRNA transcript, thereby providing an internal control based on amplifying and detecting normal abl sequence.

19. The method of claim 17, wherein the first primer is of SEQ ID NO:1, the second primer is of SEQ ID NO:5, and the probe is of SEQ ID NO:9 or SEQ ID NO:27 or is a mixture of SEQ ID NO:9 and SEQ 10 NO:27.

20. The method of claim 17, wherein the first primer is of SEQ ID NO:1, the second primer is of SEQ ID NO:5 or its RNA equivalent, and the probe is of SEQ ID NO:9 or its RNA equivalent.

21. The method of claim 17, wherein the first primer is of SEQ ID NO:1, the second primer is of SEQ ID NO:5, and the probe is of SEQ ID NO:27.

22. The method of claim 18, wherein the third primer is of SEQ ID NO:13 or its RNA equivalent, and the oligonucleotide probe that hybridizes to the amplified normal abl sequence is of SEQ ID NO:16 or its RNA equivalent or SEQ ID NO:26.

23. The method of claim 8, wherein the first primer is of SEQ ID NO:1, the first probe is of SEQ ID NO:9, and the second probe is of SEQ ID NO:16.

* * * * *